US007560610B2

(12) United States Patent
Roberts et al.

(10) Patent No.: US 7,560,610 B2
(45) Date of Patent: Jul. 14, 2009

(54) P27-DEFICIENT MOUSE EXHIBITING TISSUE HYPERTROPHY

(75) Inventors: James M. Roberts, Seattle, WA (US); Steven R. Coats, Seattle, WA (US); Matthew L. Fero, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 248 days.

(21) Appl. No.: 10/408,157

(22) Filed: Apr. 3, 2003

(65) Prior Publication Data

US 2004/0034878 A1 Feb. 19, 2004

Related U.S. Application Data

(63) Continuation of application No. 09/637,848, filed on Aug. 10, 2000, now abandoned, which is a continuation of application No. 08/656,562, filed on May 31, 1996, now abandoned, which is a continuation-in-part of application No. 08/588,595, filed on Jan. 18, 1996, now Pat. No. 5,958,769.

(51) Int. Cl.
*A01K 67/027* (2006.01)
*A01K 67/00* (2006.01)
(52) U.S. Cl. ............................... 800/18; 800/14; 800/8
(58) Field of Classification Search .................. 800/18, 800/14, 8
See application file for complete search history.

(56) References Cited

U.S. PATENT DOCUMENTS

| 5,302,706 A | 4/1994 | Smith |
| 5,958,769 A | 9/1999 | Roberts et al. |

FOREIGN PATENT DOCUMENTS

| WO | WO 95/18824 | 7/1995 |
| WO | WO 96/02140 | 2/1996 |

OTHER PUBLICATIONS

Ferrando et al. Hum. Genet. 97:91-94; 1996; Abstract.*
Deng et al. Cell 82:675-684; 1995.*
Bradley et al., "Modifying the Mouse: Design and Desire," *Biotechnology*, 10:534-539 (1992).
Brugarolas et al., "Radiation-Induced Cell Cycle Arrest Compromised by p21 Deficiency," *Nature*, 377:552-557 (1995).
Chan et al., "Identification of Human and Mouse p19, a Novel CDK4 and CDK6 Inhibitor with Homology in p16ink4", *Mol. Cell. Biol.*, 15:2682-2688 (1995).
Charreau et al., "Transgenesis in Rats: Technical Aspects and Models," *Transgenetic Res.*, 5:223-234 (1996).
Coats et al., "Requirement of the p27Kip1 for Restriction Point Control of the Fibroblast Cell Cycle", *Science*, 272:877-880 (1996).
Deng et al., "Mice Lacking P21$^{CIP1/WAF1}$ Undergo Normal Development, but Are Defective in G1 Checkpoint Control," *Cell*, 82:675-684 (1995).

Donehower et al., "Mice Deficient for p53 are Developmentally Normal but Susceptible to Spontaneous Tumours", *Nature*, 356:215-221 (1992).
Fero et al., "A Syndrome of Multiorgan Hyperplasia with Feature of Gigantism, Tumorigenesis, and Female Sterility in p27Kip1-Deficient Mice", *Cell*, 86:733-744 (1996).
Firpo et al., "Inactivation of a Cdk2 Inhibitor during Interleukin 2-Induced Proliferation of Human T Lymphocytes", *Mol. Cell. Biol.*, 14:4889-4901 (1994).
Hasty et al., "Target Frequency and Integration Pattern for Insertion and Replacement Vectors in Embryonic Stem Cells", *Mol. Cell. Biol.*, 11:4509-4517 (1991).
Kappel et al., "Regulating Gene Expression in Transgenic Animals," *Curr. Opin. Biotechnol.*, 3:548-553 (1992).
Kato et al., "Cyclic AMP-induced G1 Phase Arrest Mediated by an Inhibitor (p27Kip1) of Cyclin-Dependent Kinase 4 Activation", *Cell*, 79:487-496 (1994).
Kaushansky et al., "Promotion of Megakaryocyte Progenitor Expansion and Differentiation by the c-Mpl Ligand Trhombopoietin", *Nature*, 369:568-571 (1994).
Khare et al., "Unraveling the Mystery of HLA-B27 Association with Human Spondyloarthropathies Using Transgenic and Knock Out Mice," *Immunology*, 10:15-23 (1998).
Kiyokawa et al., "Enhanced Growth of Mice Lacking the Cyclin-Dependent Kinase Inhibitor Function of p27Kip1", *Cell*, 85:721-732 (1996).
Koff et al., "Formation and Activation of a Cyclin E-cdk2 Complex During the G1 Phase of the Human Cell Cycle", *Science*, 257:1689-1694 (1992).
Koff et al., "Negative Regulation of G1 in Mammalian Cells: Inhibition of Cyclin E-Dependent Kinase by TGF-β", *Science*, 260:536-539 (1993).
Nakayama et al., "Mice Lacking p27$^{Kip1}$ Display Increased Body Size, Multiple Organ Hyperplasia, Retinal Dysplasia, and Pituitary Tumors," *Cell*, 85:707-720 (1996).
Nakayama et al., "Disappearance of the Lymphoid System in Bcl-2 Homozygous Mutant Chimeric Mice", *Science*, 261:1584-1588 (1993).
Nourse et al., "Interleukin-2-mediated Elimination of the p27Kip1 Cyclin-dependent Kinase Inhibitor Prevented by Rapamycin", *Nature* 372:570-573 (1994).
Ohtsubo et al., "Cyclin-Dependent Regulation of G1 in Mammalian Fibroblasts", *Science*, 259:1908-1912 (1993).

(Continued)

*Primary Examiner*—Fereydoun G Sajjadi
(74) *Attorney, Agent, or Firm*—Townsend and Townsend and Crew LLP

(57) ABSTRACT

Hypercellular nonhuman organisms have functionally inactivated expression of a cyclin inhibitor gene, especially p27. The growth rate of nonhuman organisms are increased such that a desired size is attained more quickly than as compared to nonvariant organisms. Inhibitors of the p27 cyclin dependent kinase inhibitor protein or sequences encoding the protein modulate vertebrate cell cycle progression and increase the proportion of dividing cells to non-dividing cells in a population of treated cells. As the proportion of dividing cells increases, the cell population, e.g., hematopoietic progenitor (stem) cells, is more efficiently used for gene therapy applications. Transgenic animals and plants, and knockout alleles are provided.

8 Claims, 7 Drawing Sheets

OTHER PUBLICATIONS

Polyak et al., "Cloning of p27Kip1, a Cyclin-Dependent Kinase Inhibitor and a Potential Mediator of Extracellular Antimitogenic Signals", *Cell*, 78:59-66 (1994).

Polyak et al., "p27Kip1, a Cyclin-Cdk Inhibitor, Links Transforming Growth Factor-β and Contact Inhibition to Cell Cycle Arrest", *Genes Dev.*, 8:9-22 (1994).

Rahemtulla et al., "Normal Development and Function of CD8+ Cells but Markedly Decreased Helper Cell Activity in Mice Lacking CD4", *Nature*, 353:180-184 (1991).

Raviprakash et al., "Inhibition of Dengue Virus by Novel, Modified Antisense Oligonucleotides", *J. Virol.*, 69:69-74 (1995).

Ravitz et al., "Transforming Growth Factor β-induced Activation of Cyclin E-cdk2 Kinase and Down-Regulation of p27Kip1 in C3H 10T½ Mouse Fibroblasts", *Can. Res.*, 55:1413-1416 (1995).

Resnitzky et al., "Different Roles for Cyclins D1 and E in Regulation of the G1-to-S Transition", *Mol. Cell. Biol.*, 15:3463-3469 (1995).

Rivard et al., "Abrogation of p27Kip1 by cDNA Antisense Suppresses Quiescence (G0 State) in Fibroblasts", *J. Biol. Chem.*, 271:18337-18341 (1996).

Serrano et al., "A New Regulatory Motif in Cell-Cycle Control Causing Specific Inhibition of Cyclin D/CDK4", *Nature*, 366:704-707 (1993).

Sherr et al., "Inhibitors of Mammalian G1 Cyclin-Dependent Kinases", *Genes Dev.*, 9:1149-1163 (1995).

Shulman et al., "Homologous Recombination in Hybridoma Cells: Dependence on Time and Fragment Length", *Mol. Cell. Biol.*, 10:4466-4472 (1990).

Slingerland et al., "A Novel Inhibitor of Cyclin-Cdk Activity Detected in Transforming Growth Factor β-Arrested Epithelial Cells", *Mol. Cell. Biol.*, 14:3683-3694 (1994).

Sorrentino et al., "Selection of Drug-Resistant Bone Marrow Cells in Vivo After Retroviral Transfer of Human MDR1", *Science*, 257:99-103 (1992).

Toyoshima et al., "p27, a Novel Inhibitor of G1 Cyclin-Cdk Protein Kinase Activity, is Related to p21", *Cell*, 78:67-74 (1994).

Tyers, "The Cyclin-Dependent Kinase Inhibitor p40$^{SIC1}$ Imposes the Requirement for Cln G1 Cyclin Function at Start," *Proc. Natl. Acad. Sci. USA*, 93:7772-7776 (1996).

Zhuang et al., "The Helix-Loop-Helix Gene E2A Is Required for B Cell Formation", *Cell*, 79:875-884 (1994).

Aoki, K. et al., "Liposome-mediated in vivo gene transfer of antisense K-*ras* construct inhibits pancreatic tumor dissemination in the murine peritoneal cavity," *Cancer Res.*, 55:3810-3816 (Sep. 1, 1995).

Campbell, K. and Wilmut, I. et al., "Totipotency or multipotentiality of cultured cells: Applications and progress," *Theriogenology*, 47:63-72 (1997).

Nakanishi, M. et al., "Exit from $G_0$ and entry into the cell cycle of cells expressing p21$^{Sdi1}$ antisense RNA," *Proc. Natl. Acad. Sci. USA*, 92:4352-4356 (May 1995).

Pietenpol, J. et al., "Assignment of the human *p27$^{Kip1}$* gene to 12p13 and its analysis in leukemias," *Cancer Res.*, 55:1206-1210 (Mar. 15, 1995).

Southgate, J. et al., "Loss of cyclin-dependent kinase inhibitor genes and chromosome 9 karyotypic abnormalities in human bladder cancer cell lines," *Br. J. Cancer*, 72:1214-1218 (1995).

Wigley, P. et al., "Site-specific transgene insertion: an approach," *Reprod. Fertil. Dev.*, 6:585-588 (1994).

Wolf, G. and Stahl, R., "Angiotensin II-stimulated hypertrophy of LLC-PK$_1$ cells depends on the induction of the cyclin-dependent kinase inhibitor p27$^{Kip1}$," *Kidney Int.*, 50:2112-2119 (1996).

\* cited by examiner p27 Immunoblot

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 15 base pairs
      (B) TYPE: nucleic acid
      (C) STRANDEDNESS: single
      (D) TOPOLOGY: linear

```
        (ii) MOLECULE TYPE: other nucleotide (xi) SEQUENCE DESCRIPTION: SEQ ID NO: 1:

UGGCUCUCCU GCGCC                                                    15

(2) INFORMATION FOR SEQ ID NO: 2:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleotide (xi) SEQUENCE DESCRIPTION: SEQ ID NO: 2:

UCCCUUUGGC GCGCC                                                    15

(2) INFORMATION FOR SEQ ID NO: 3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleotide (xi) SEQUENCE DESCRIPTION: SEQ ID NO: 3:

GCGUCUGCUC CACAG                                                    15

(2) INFORMATION FOR SEQ ID NO: 4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleotide (xi) SEQUENCE DESCRIPTION: SEQ ID NO: 4:

GCAUCCCCUG UGCAG                                                    15

(2) INFORMATION FOR SEQ ID NO: 5:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

Leu Ala Gln Glu Ser
1               5

(2) INFORMATION FOR SEQ ID NO: 6:

(i) SEQUENCE CHARACTERISTICS:
        (A) LENGTH: 15 base pairs
        (B) TYPE: nucleic acid
        (C) STRANDEDNESS: single
        (D) TOPOLOGY: linear
```

-continued

```
        (ii) MOLECULE TYPE: other nucleotide (xi) SEQUENCE DESCRIPTION: SEQ ID NO: 6:

CTGGCGCAGG AGAGC                                                    15

(2) INFORMATION FOR SEQ ID NO: 7:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: other nucleotide (xi) SEQUENCE DESCRIPTION: SEQ ID NO: 7:

CTTGCACAAG AATCA                                                    15

(2) INFORMATION FOR SEQ ID NO: 8:

(i) SEQUENCE CHARACTERISTICS:
            (A) LENGTH: 66 base pairs
            (B) TYPE: nucleic acid
            (C) STRANDEDNESS: single
            (D) TOPOLOGY: linear (ii) MOLECULE TYPE: other nucleotide (xi) SEQUENCE DESCRIPTION: SEQ ID NO: 8:

TAAAGGCACC GCCTGGCGAC TACCGCTGAC GTCCTGTGAT TCTTGTGCAA GCACCTTGCA    60

GGCGCT                                                              66

(2) INFORMATION FOR SEQ ID NO: 9:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 9:

Leu Ala Gln Glu Ser Gln Asp
1               5

(2) INFORMATION FOR SEQ ID NO: 10:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleotide (xi) SEQUENCE DESCRIPTION: SEQ ID NO: 10:

CCTTCTATGG CCTCCTTGAC G                                             21

(2) INFORMATION FOR SEQ ID NO: 11:

(i) SEQUENCE CHARACTERISTICS:
            (A) LENGTH: 24 base pairs
            (B) TYPE: nucleic acid
            (C) STRANDEDNESS: single
            (D) TOPOLOGY: linear
```

-continued (ii) MOLECULE TYPE: other nucleotide (xi) SEQUENCE DESCRIPTION: SEQ ID NO: 11:

TTCTTACCGA AAGGGACACT AATC                             24

(2) INFORMATION FOR SEQ ID NO: 12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleotide (xi) SEQUENCE DESCRIPTION: SEQ ID NO: 12:

TGGAACCCTG TGCCATCTCT AT                               22

(2) INFORMATION FOR SEQ ID NO: 13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleotide (xi) SEQUENCE DESCRIPTION: SEQ ID NO: 13:

GAGCAGACGC CCAAGAAGC                                   19

P27-DEFICIENT MOUSE EXHIBITING TISSUE HYPERTROPHY

CROSS-REFERENCE TO RELATED APPLICATION

This application is a continuation of application Ser. No. 09/637,848, filed Aug. 10, 2000, now abandoned, which is a continuation of application Ser. No. 08/656,562, filed May 31, 1996, now abandoned, which is a continuation-in-part of application Ser. No. 08/588,595 filed Jan. 18, 1996, now U.S. Pat. No. 5,958,769, issued Sep. 28, 1999, each of which is incorporated herein by reference.

GOVERNMENT SUPPORT

The U.S. government may have certain rights in the invention pursuant to Grant No. CA 61352 received from the U.S. National Institutes of Health.

BACKGROUND OF THE INVENTION

Mammalian cells can shift from a proliferating state to a quiescent state only during a brief window of the cell cycle. Temin, *J. Cell. Phys.* 78:161 (1971). Thus, depending on their position in the cell cycle, cells deprived of mitogens such as those present in serum will undergo immediate cell cycle arrest, or they will complete mitosis and arrest in the next cell cycle. The transition from mitogen-dependence to mitogen-independence occurs in the mid- to late-G1 phase of the cell cycle. Pardee, *Proc. Natl. Acad. Sci.* 71:1286 (1974), showed that many different anti-mitogenic signals cause the cell cycle to arrest at a kinetically common point, and further showed that the cell cycle becomes unresponsive to all of these signals at approximately the same time in mid- to late-G1. This point was named the restriction point, or R point.

Time-lapse cinematography of mitotically proliferating single cells has also been used to precisely map the timing of the cell cycle transition to mitogen-independence. This confirmed that mitogen depletion or other growth inhibitory signals cause post-mitotic, early-G1 cells to immediately exit the cell cycle, and that cell cycle commitment (autonomy from mitogenic signals), occurs in mid-G1 (Larsson et al., *J. Cell. Phys.* 139:477 (1989), and Zetterberg et al., *Proc. Natl. Acad. Sci. USA* 82:5365 (1985)). Together these observations show that the mitogen-dependent controls on cell proliferation are linked to cell cycle progression.

Transit through G1 and entry into S phase requires the action of cyclin-dependent kinases (Cdks) (Sherr, *Cell* 79:551 (1994)). Growth inhibitory signals have been shown to prevent activation of these Cdks during G1 (Serrano et al., *Nature* 366:704 (1993); Hannon and Beach, *Nature* 371: 257 (1994); El-Deiry et al., *Cell* 75:89 (1993); Xiong et al., *Nature* 366:701 (1993); Polyak et al., *Cell* 78:59 (1994); Toyashima and Hunter, ibid., p. 67; Lee et al., *Genes & Dev.* 9:639 (1995); Matsuoka et al., ibid., p. 650; Koff et al., Science 260:536 (1993)). The catalytic activity of Cdks is known to be regulated by two general mechanisms, protein phosphorylation and association with regulatory subunits (Gould et al., *EMBO J.* 10:3297 (1991); Solomon et al., ibid., 12:3133 (1993); Solomon et al., *Mol. Biol. Cell* 3:13 (1992); Jeffrey et al., *Nature* 376:313 (1995); Morgan, *Nature* 374:131 (1995)). Among the regulatory subunits, the association of Cdks with inhibitory CKI subunits (Cyclin-dependent Kinase Inhibitors) has been most closely correlated with the effect of mitogen depletion on cell proliferation and Cdk activity.

The CKI directly implicated in mitogen-dependent Cdk regulation is p27Kip1 (Polyak et al., *Cell* 78:59 (1994); Toyashima and Hunter, ibid., p. 677). The p27 protein accumulates to high levels in quiescent cells, and is rapidly destroyed after quiescent cells are re-stimulated with specific mitogens (Nourse et al., *Nature* 372:570 (1994); Kato et al., *Cell* 79:487 (1994)). Moreover, constitutive expression of p27 in cultured cells causes the cell cycle to arrest in G1 (Polyak supra, Toyashima and Hunter, supra)

Gene therapy is proposed for treating and preventing a wide variety of acquired and hereditary diseases, such as infectious diseases, cancer, etc. and relies on the efficient delivery of therapeutic genes to target cells. Most of the somatic cells that have been targeted for gene therapy, e.g., hematopoietic cells, skin fibroblasts and keratinocytes, hepatocytes, endothelial cells, muscle cells and lymphocytes, are normally non-dividing. Retroviral vectors, which are the most widely used vectors for gene therapy, unfortunately require cell division for effective transduction (Miller et al., *Mol. Cell. Biol.* 10:4239-4242 (1990)). This is also true with other gene therapy vectors such as the adeno-associated vectors (Russell et al., *Proc. Natl. Acad. Sci. USA* 91: 8915-8919 (1994); Alexander et al., *J. Virol.* 68: 8282-8287 (1994); Srivastrava, *Blood Cells* 20: 531-538 (1994)). The majority of stem cells, a preferred target for many gene therapy treatments, are normally not proliferating. Thus, the efficiency of transduction is often relatively low, and the gene product may not be expressed in therapeutically or prophylactically effective amounts. This has led investigators to develop techniques such as pretreatment with 5-fluorouracil, infection in the presence of cytokines, and extending the vector infection period to increase the likelihood that stem cells are dividing during infection, but these have met with limited success.

In one aspect, what is needed in the art is a method for improving the efficiency of gene transfer that is useful for a wide variety of gene therapy applications. For example, what is needed is a means to improve transduction efficiency into a wide variety of vertebrate cells with vectors that can transduce only dividing cells by controlling key molecular events in the cell cycle commitment through the Restriction point and thus cell cycle progression.

Gene targeting, mediated by homologous recombination between a targeting polynucleotide construct and a homologous chromosomal sequence, has been used to disrupt several genes, including the HPRT gene, β2-microglobulin gene, int-2 proto-oncogene, and the fos proto-oncogene (Thomas and Cappechi (1987) *Cell* 51: 503; Zijlstra et al. (1989) *Nature* 342: 435; Mansour et al. (1988) *Nature* 336: 348; and Johnson et al. (1989) *Science* 245: 1234: Adair et al. (1989) *Proc. Natl. Acad. Sci (U.S.A.)* 86:4574; Capecchi, M. (1989) *TIG* 5:70; Capecchi, M. (1989) *Science* 244:1288). Mansour et al. (1988) op.cit. have described homologous targeting constructs that include a HSV tk gene that permits negative selection against nonhomologous integration events in conjunction with positive selection for integrated transgenes.

Transgenic nonhuman mammalian cells and transgenic nonhuman animals which harbor one or more inactivated cyclin inhibitor genes required for induction or inhibition of cell proliferation, such as the cyclin regulator proteins p27, p16, p14, p18, p21, and the like are desirable as experimental model systems and as hosts for expression of transgenes encoding heterologous (e.g., human) cyclin-related proteins. Such cells and animals also have cell proliferation advantages which are desired in industry and agriculture, such as increased cell proliferation, increased animal size, and increased growth rate. Lonberg (WO92/03918) describes construction of vectors for targeting endogenous immunoglobulin loci and inactivation of endogenous immunoglobulin genes with such targeting vectors. Rahemtulla et al. (1991) *Nature* 353: 180, describes disruption of an endogenous murine CD4 gene by homologous gene targeting in embryonic stem cells. Jasin et al. (1990) *Genes Devel.* 4: 157, report targeting the human CD4 gene in a T lymphoma cell line by epitope addition. Koh et al. (1992) *Science* 256: 1210, report disruption of an endogenous murine CD8 gene by homologous gene targeting in ES cells. Molina et al. (1992) op.cit., describes disruption of the murine 1 ck gene, which encodes a tyrosine kinase implicated in signal transduction by CD4 and CD8. Grusby et al. (1991) *Science* 253: 1417, describes disruption of the MHC Class II $A^b$ beta gene by gene targeting in mice; the resultant targeted mice are reported to be depleted of $CD4^+$ lymphocytes. Nakayama et al. (1993) *Science* 261: 1584 report making chimeric knockout mice wherein some somatic cells of the chimera lack functional bcl-2 genes, and germline transmission of the knockout allele.

Organisms having a functionally inactivated endogenous cyclin inhibitor gene (and optionally also harboring a transgene which expresses a heterologous (i.e., derived from a different species) or mutant variant cyclin inhibitor gene product) would be useful as models for studying disease pathogenesis and fundamental cell biology, as well as providing useful models for screening for novel therapeutic agents to treat diseases related to abnormal cell proliferation.

Based on the foregoing, it is clear that a need exists for nonhuman cells and organisms harboring one or more functionally inactivated endogenous cyclin inhibitor genes, and optionally also harboring a transgene encoding a heterologous cyclin inhibitor polypeptide or mutant variant cyclin inhibitor polypeptide which is expressed in at least a subset of host cells. Thus, it is an object of the invention herein to provide targeting transgenes for inactivating, by homologous recombination, endogenous cyclin inhibitor genes, particularly the p27 gene. It is also an object of the invention to provide methods to produce transgenic nonhuman cells and transgenic nonhuman animals harboring correctly targeted homologously recombined transgenes of the invention. The methods may also be used to inactivate p27 genes and/or other cyclin inhibitor genes in cells explanted from a patient (e.g., for ex vivo gene therapy), such as to impart to the resultant targeted cells an altered cell proliferation phenotype.

Methods for controlling the expression of certain plant genes can be used to modify a plant's phenotype as desired, such as controlling the rate or time at which fruit ripening occurs or potentially even the growth rate of a plant. One way to control expression of endogenous plant genes is the inhibition of specific gene expression by antisense suppression (U.S. Pat. Nos. 5,457,281, 5,453,566, 5,365,015, 5,254,800, 5,107,065, and 5,073,676), and an alternative method to inhibit expression of specific genes is sense suppression (U.S. Pat. Nos. 5,283,184, 5,231,020, and 5,034,323), each of said patents being incorporated herein by reference.

SUMMARY OF THE INVENTION

The present invention provides compositions which comprise inhibitors of p27 that specifically increase the proportion of dividing cells to non-dividing cells in a population of cells. The inhibitors can substantially decrease or eliminate expression of p27 protein, thereby permitting activation of cyclin Cdk complexes, for example, cyclin E-Cdk2 and/or cyclin A-Cdk2 complexes. Particularly useful are oligonucleotide inhibitors of p27, such as triplex forming oligonucleotides, an antisense oligonucleotides, and ribozymes.

In another embodiment the invention also provides isolated vertebrate cell populations which have been treated with a p27 inhibitor and have an increased proportion of dividing cells to non-dividing cells relative to the proportion in a population of untreated cells. Said dividing cells, e.g., hematopoietic progenitor cells, are particularly useful as targets of gene therapy, including the use of viral vectors that preferentially transduce dividing cells. Thus, the invention provides a method for increasing the efficiency of gene therapy techniques by increasing the number of cells which can be transduced and thereby increasing the availability of a desired gene product.

In other embodiments the invention provides methods for increasing the proportion of dividing cells in a vertebrate cell population. A population of cells is exposed to a p27 inhibitor in an amount sufficient to increase the proportion of dividing cells to non-dividing cells relative to said proportion in a population of untreated cells. Such cell population can be a substantially non-dividing or terminally differentiated primary cell population, including, e.g., fibroblasts, osteoblasts, myeloblasts, neurons or epithelial cells. Isolated hematopoietic progenitor cells are particularly useful in the present methods. The cells can be exposed to the inhibitor either in vitro or in vivo. When performed in vitro, the method can further comprise the step of administering the exposed cells to a host, particularly when the exposed cells have been transduced to express a desired gene. Thus, the method provides for increasing the efficiency of transducing a vertebrate cell population with a viral vector encoding a gene product of interest. The target cells, e.g., mammalian hematopoietic progenitor cells, are exposed to a p27 inhibitor in an amount sufficient to increase the percentage of dividing cells, and contacting the treated cells to a viral vector encoding the gene product of interest.

In a broad aspect of the invention is provided a method for producing hypertrophic organisms (i.e., organisms of enhanced size, including organisms exhibiting hypercellularity and/or hyperplasticity) comprising functionally inactivating expression of at least one cyclin inhibitor gene (which includes CDK inhibitor genes) in the organism. In a related aspect the invention provides a method for increasing the growth rate of an organism such that a desired size is attained more quickly than as compared to nonvariant organisms. In one embodiment, the non-human organism is an animal, such as a nonhuman mammal (e.g., mouse, rat, sheep, pig, cows, rabbit, and the like), fish (e.g., trout, salmon, catfish and the like), birds (e.g., poultry) etc., or a plant. In an embodiment, the cyclin inhibitor gene is a mammalian p27 gene. Generally, the method employs germline transgenes or germline structurally disrupted cyclin inhibitor gene alleles generated by homologous recombination with a targeting construct.

In one aspect of the invention, targeting constructs are provided which contain at least one portion having a sequence that is substantially homologous to a sequence present in or flanking a cyclin inhibitor gene locus (which includes CDK inhibitor gene loci) and which, when integrated at the corresponding cyclin inhibitor gene locus, functionally inactivate expression of cyclin inhibitor protein encoded by the gene locus. Such targeting constructs, or portions thereof, integrate at the cyclin inhibitor gene locus by homologous recombination between the endogenous gene locus and the targeting construct, and cells harboring correctly integrated targeting constructs are selected for and identified by screening according to the methods described herein. In one embodiment, the targeting constructs delete all or a portion of an endogenous cyclin inhibitor gene by a "hit-and-run" strategy, wherein the resultant functionally inactivated cyclin inhibitor locus comprises a deletion and does not comprise an integrated selectable marker. In an alternative embodiment, an endogenous cyclin inhibitor gene is functionally inactivated by a targeting construct which inserts a sequence, typically into a coding sequence (i.e., exon), wherein the resultant inactivated cyclin inhibitor gene is substantially incapable of expressing a functional cyclin inhibitor protein. The invention also provides targeting constructs which functionally inactivate an endogenous cyclin inhibitor gene by targeted site-specific point mutation(s), such as to create a missense or nonsense codon in a coding sequence or ablate a splice signal or transcriptional element sequence. In a preferred embodiment of the invention, an endogenous cyclin inhibitor locus, such as a cyclin inhibitor locus, e.g., that encoding p27, is functionally inactivated.

The invention also provides targeting constructs that contain at least one portion having a sequence that is substantially homologous to a sequence present in or flanking a cyclin inhibitor gene locus, and which serves as a template for gene conversion of the corresponding endogenous cyclin inhibitor gene locus. Such targeted gene conversion results in the converted (i.e., mutated by gene conversion) endogenous cyclin inhibitor locus being functionally inactivated and incapable of directing the efficient expression of functional cyclin inhibitor protein. The invention also provides cells and non-human animals and plants harboring inactivated cyclin inhibitor genes that result from correctly targeted gene conversion. Nucleotide sequences that result from correctly targeted gene conversion generally are not naturally-occurring sequences in the genome(s) of mammals, so a sequence resulting from targeted gene conversion is generally distinguishable from naturally-occurring mutant cyclin inhibitor alleles in the host cell or host animal species. A preferable cyclin inhibitor gene for functional disruption by gene conversion is a p27 gene.

The invention also provides targeting constructs which replace, by homologous recombination, at least a portion of an endogenous cyclin inhibitor gene with a corresponding portion of a heterologous cyclin inhibitor gene. Such replacements may be partial, yielding a hybrid cyclin inhibitor gene composed partially of endogenous coding and/or regulatory sequences and partially of heterologous cyclin inhibitor gene sequences, or total, wherein the endogenous cyclin inhibitor gene is replaced by a heterologous cyclin inhibitor gene. In some embodiments, the heterologous cyclin inhibitor gene sequences comprise deletions of nonessential sequences, such as intronic sequences, and are referred to as cyclin inhibitor minigenes. For example, the invention provides a human or murine cyclin inhibitor minigene which can be transcribed and translated in a nonhuman host to produce a functional human cyclin inhibitor protein which is developmentally expressed in the same way as an endogenous host cyclin inhibitor gene in a naturally occurring, nontransgenic animal. Such a human cyclin inhibitor minigene may comprise part of a targeting construct or may be separately introduced as a transgene.

The invention also provides nonhuman animals and cells which harbor at least one integrated targeting construct that functionally inactivates an endogenous cyclin inhibitor gene locus, typically by deleting or mutating a genetic element (e.g., exon sequence, splicing signal, promoter, enhancer) that is required for efficient functional expression of a complete gene product. In one embodiment, disruption of an endogenous cyclin inhibitor gene locus may be accomplished by replacement of a portion of the endogenous cyclin inhibitor gene with a portion of a heterologous cyclin inhibitor gene (e.g., a human p27 gene sequence) by homologous recombination or gene conversion. In an alternative embodiment, a targeting construct is employed to functionally disrupt an endogenous cyclin inhibitor gene by homologous recombination, and a transgene encoding and expressing a heterologous molecule is separately introduced into the host genome at a nonhomologous site.

The invention also provides transgenic nonhuman animals and plants harboring at least one endogenous cyclin inhibitor gene that is inactivated by a targeted genetic modification produced by contacting the endogenous cyclin inhibitor gene with a targeting construct of the invention. Such contacting of a targeting construct with an endogenous cyclin inhibitor sequence generally involves electroporation, lipofection, microinjection, calcium phosphate precipitation, biolistics, or other polynucleotide transfer method known in the art.

The invention also provides cells that express an endogenous cyclin inhibitor gene, but which have portions of the expressed endogenous cyclin inhibitor gene deleted or mutated. For example but not limitation, an endogenous cyclin inhibitor gene can be modified by deleting specific, predetermined exons from germline DNA with one or more targeting constructs, with preferable deletions being those having boundaries approximately the same as boundaries for structural and/or functional domains of the cyclin inhibitor protein. In an alternative embodiment, predetermined exons or structural domains of an endogenous cyclin inhibitor gene may be replaced, by homologous targeting, with corresponding portions of a heterologous cyclin inhibitor gene to generate a hybrid cyclin inhibitor gene.

The invention also provides organisms, such as transgenic nonhuman animals, that have at least one inactivated endogenous cyclin inhibitor gene, and preferably are homozygous for inactivated cyclin inhibitor alleles, and which are substantially incapable of directing the efficient expression of endogenous cyclin inhibitor. For example, in a preferred embodiment, a transgenic nonhuman mammal is homozygous for inactivated endogenous cyclin inhibitor alleles and is substantially incapable of producing cyclin inhibitor encoded by a endogenous (i.e., naturally-occurring) cyclin inhibitor gene.

The invention also provides vectors, methods, and compositions useful for suppressing the expression of one or more species of cyclin inhibitor gene products, without disrupting an endogenous cyclin inhibitor locus. Such methods are useful for suppressing expression of one or more endogenous cyclin inhibitor gene products; and in a variation can be conditionally controlled by use of an operably-linked transcriptional regulatory sequence which can conditionally express (e.g., in the presence of an inducer, in a tissue-specific manner, in a developmental stage-specific manner, or the like) the suppression antisense transcript, permitting the regulated expression (or suppression) of one or more cyclin inhibitor gene products. Unlike genetic disruption of an endogenous cyclin inhibitor locus, suppression of cyclin inhibitor gene product expression does not require the time-consuming breeding that is needed to establish transgenic animals homozygous for a disrupted endogenous locus. An additional advantage of suppression as compared to endogenous cyclin inhibitor gene disruption is that, in certain embodiments, suppression is reversible within an individual animal. For example, cyclin inhibitor suppression may be accomplished with: (1) transgenes encoding and expressing antisense RNA that specifically hybridizes to an endogenous cyclin inhibitor gene sequence, (2) antisense oligonucleotides that specifically hybridize to an endogenous cyclin inhibitor gene sequence, and (3) intracellular proteins that bind specifically to an endogenous cyclin inhibitor polypeptide and inhibit its function.

In an aspect, the invention provides a method for producing organisms having reduced size and/or cell number, comprising effecting hyperphysiological expression of at least one cyclin inhibitor gene. In a related embodiment, the invention provides expression transgenes which comprise a transcriptional regulatory sequence operably linked to a cyclin inhibitor gene encoding sequence, which can effect expression of the cyclin inhibitor gene product and retard or inhibit cell proliferation. Such transgenes, when expressed in a nonhuman animal, can yield animals having reduced morphologic characteristics (e.g., smaller body size, reduced cellularity of organs, atypical body plan dimensions), and other related cell proliferation phenotypes.

The invention also provides transgenes which encode a cyclin inhibitor gene product in a nonhuman host species. Such transgenes typically comprise a cyclin inhibitor gene expression cassette, wherein a linked promoter and, preferably, an enhancer drive expression of structural sequences encoding the cyclin inhibitor protein. For example, the invention provides transgenes which comprise a constitutive murine enhancer and promoter linked to structural sequences that encode a cyclin inhibitor protein. Transgenic mice harboring such transgenes express cyclin inhibitor in developmental patterns and at levels which are comparable with expression patterns and levels of the mouse gene from which the promoter and enhancer were derived in normal nontransgenic mice. In one aspect, the polynucleotide sequence encoding the heterologous cyclin inhibitor molecule is operably linked to cis-acting transcriptional regulatory regions (e.g., promoter, enhancer) so that a cyclin inhibitor protein is expressed in a subset of cells. Transgenes encoding cyclin inhibitor proteins may be targeted adjacent to endogenous transcriptional regulatory sequences, so that the operable linkage of a regulatory sequence occurs upon integration of the transgene into a targeted endogenous chromosomal location.

In embodiments where it is desired to overexpress a cyclin inhibitor gene, at least one cyclin inhibitor protein may be encoded and expressed from a transgene(s) in transgenic nonhuman organisms. Such transgenes may be integrated in a nonhomologous location in a chromosome of the nonhuman animal, or may be integrated by homologous recombination or gene conversion into a nonhuman gene locus.

BRIEF DESCRIPTION OF THE DRAWINGS

FIG. 1 shows that p27 is required for cell cycle withdrawal, where

FIG. 2 shows that enforced p27 expression reverses the p27 antisense effect in serum starved cells, where

DEFINITIONS

Figure 1A:
FIG. 1A is a p27 immunoblot analysis of extracts from control proliferating Balb/c-3T3 cells (Hi), subconfluent serum starved Balb/c-3T3 cells (Low) and subconfluent Balb/c-3T3 cells serum starved for 24 h following lipofection with either p27 mismatch (MS) or antisense (AS) oligonucleotides.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

"Cyclin inhibitor protein" as used herein, refers to a protein which binds to and inactivates a cyclin-dependent kinase (CDK) or a related protein in the cyclin pathway in a cell. The p27 protein is an example of a cyclin inhibitor protein. A cyclin inhibitor gene as used herein is a polynucleotide sequence which encodes a cyclin inhibitor protein.

As used herein, the term "cyclin inhibitor gene" or "cyclin inhibitor gene locus" refers to a region of a chromosome spanning all of the exons which potentially encode a cyclin inhibitor polypeptide and extending through flanking sequences (e.g., including promoters, enhancers, etc.) that participate in cyclin inhibitor protein expression. Essentially any gene encoding a cyclin inhibitor protein may be targeted. A particularly preferred gene is the p27 gene, which can be targeted, and, if desired, replaced with a cognate heterologous gene or minigene.

The term "structurally disrupted" as used herein means that a gene locus comprises at least one mutation or structural alteration such that the disrupted gene is incapable of directing the efficient expression of a functional gene product. The term "functionally inactivated" means a gene locus that is either not expressed or is incapable of expressing a gene product. Functional inactivation may result from structural disruption and/or interruption of expression at either the level of transcription or translation. Functional inactivation of an endogenous cyclin inhibitor gene, such as a p27 gene, may also be produced by other methods, e.g., antisense polynucleotide gene suppression.

The term "corresponds to" is used herein to mean that a polynucleotide sequence that shares identity to all or a portion of a reference polynucleotide sequence. The term "complementary to" is used herein to mean that the sequence is complementary to all or a portion of a reference polynucleotide sequence.

The terms "substantially corresponds to", "substantially homologous", or "substantial identity" as used herein denotes a characteristic of a nucleic acid sequence, wherein a nucleic acid sequence has at least about 70 percent sequence identity as compared to a reference sequence, typically at least about 85 percent sequence identity, and preferably at least about 95 percent sequence identity as compared to a reference sequence. The percentage of sequence identity is calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least about 30 nucleotides long, and preferably at least about 50 to 100 nucleotides long. "Substantially complementary" as used herein refers to a sequence that is complementary to a sequence that substantially corresponds to a reference sequence. In general, targeting efficiency increases with the length of the targeting transgene portion (i.e., homology region) that is substantially complementary to a reference sequence present in the target DNA (i.e., crossover target sequence). In general, targeting efficiency is optimized with the use of isogenic DNA homology clamps, although it is recognized that the presence of various recombinases may reduce the degree of sequence identity required for efficient recombination.

The term "nonhomologous sequence", as used herein, has both a general and a specific meaning; it refers generally to a sequence that is not substantially identical to a specified reference sequence, and, where no particular reference sequence is explicitly identified, it refers specifically to a sequence that is not substantially identical to a sequence of at least about 50 contiguous bases at a targeted endogenous cyclin inhibitor gene, such as a p27 gene.

Specific hybridization is defined herein as the formation of hybrids between a targeting transgene sequence (e.g., a polynucleotide of the invention which may include substitutions, deletion, and/or additions) and a specific target DNA sequence (e.g., a p27 gene sequence), wherein a labeled targeting transgene sequence preferentially hybridizes to the target such that, for example, a single band corresponding to a restriction fragment of a genomic cyclin inhibitor gene can be identified on a Southern blot of DNA prepared from cells using said labeled targeting transgene sequence as a probe. It is evident that optimal hybridization conditions will vary depending upon the sequence composition and length(s) of the targeting transgene(s) and endogenous target(s), and the experimental method selected by the practitioner. Various guidelines may be used to select appropriate hybridization conditions (see, Maniatis et al., *Molecular Cloning: A Laboratory Manual* (1989), 2nd Ed., Cold Spring Harbor, N.Y. and Berger and Kimmel, *Methods in Enzymology, Volume* 152, *Guide to Molecular Cloning Techniques* (1987), Academic Press, Inc., San Diego, Calif., which are incorporated herein by reference.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. As used herein, laboratory strains of rodents which may have been selectively bred according to classical genetics are considered naturally-occurring animals.

The term "homologue" as used herein refers to a gene sequence that is evolutionarily and functionally related between species.

As used herein, the term "targeting construct" refers to a polynucleotide which comprises: (1) at least one homology region having a sequence that is substantially identical to or substantially complementary to a sequence present in a host cell endogenous cyclin inhibitor gene locus, and (2) a targeting region which becomes integrated into an host cell endogenous cyclin inhibitor gene locus by homologous recombination between a targeting construct homology region and said endogenous cyclin inhibitor gene locus sequence. If the targeting construct is a "hit-and-run" or "in-and-out" type construct (Valancius and Smithies (1991) *Mol. Cell. Biol.* 11: 1402; Donehower et al. (1992) *Nature* 356: 215; (1991) *J.* *NIH Res.* 3: 59; which are incorporated herein by reference), the targeting region is only transiently incorporated into the endogenous cyclin inhibitor gene locus and is eliminated from the host genome by selection. A targeting region may comprise a sequence that is substantially homologous to an endogenous cyclin inhibitor gene sequence and/or may comprise a nonhomologous sequence, such as a selectable marker (e.g., neo, tk, gpt). The term "targeting construct" does not necessarily indicate that the polynucleotide comprises a gene which becomes integrated into the host genome, nor does it necessarily indicate that the polynucleotide comprises a complete structural gene sequence. As used in the art, the term "targeting construct" is synonymous with the term "targeting transgene" as used herein.

The terms "homology region" and "homology clamp" as used herein refer to a segment (i.e., a portion a targeting construct having a sequence that substantially corresponds to, or is substantially complementary to, a predetermined endogenous cyclin inhibitor gene sequence, which can include sequences flanking said cyclin inhibitor gene. A homology region is generally at least about 100 nucleotides long, preferably at least about 250 to 500 nucleotides long, typically at least about 1000 nucleotides long or longer. Although there is no demonstrated theoretical minimum length for a homology clamp to mediate homologous recombination, it is believed that homologous recombination efficiency generally increases with the length of the homology clamp. Similarly, the recombination efficiency increases with the degree of sequence homology between a targeting construct homology region and the endogenous target sequence, with optimal recombination efficiency occurring when a homology clamp is isogenic with the endogenous target sequence. The terms "homology clamp" and "homology region" are interchangeable as used herein, and the alternative terminology is offered for clarity, in view of the inconsistent usage of similar terms in the art. A homology clamp does not necessarily connote formation of a base-paired hybrid structure with an endogenous sequence. Endogenous cyclin inhibitor gene sequences that substantially correspond to, or are substantially complementary to, a transgene homology region are referred to herein as "crossover target sequences" or "endogenous target sequences."

As used herein, the term "correctly targeted construct" refers to a portion of the targeting construct which is integrated within or adjacent to an endogenous crossover target sequence, such as a portion of an endogenous p27 gene locus. It is possible to generate cells having both a correctly targeted transgene(s) and an incorrectly targeted transgene(s). Cells and animals having a correctly targeted transgene(s) and/or an incorrectly targeted transgene(s) may be identified and resolved by PCR and/or Southern blot analysis of genomic DNA.

As used herein, the term "targeting region" refers to a portion of a targeting construct which becomes integrated into an endogenous chromosomal location following homologous recombination between a homology clamp and an endogenous cyclin inhibitor gene, such as a p27 gene sequence. Typically, a targeting region is flanked on each side by a homology clamp, such that a double-crossover recombination between each of the homology clamps and their corresponding endogenous cyclin inhibitor gene sequences results in replacement of the portion of the endogenous cyclin inhibitor gene locus by the targeting region; in such double-crossover gene replacement targeting constructs the targeting region can be referred to as a "replacement region". However, some targeting constructs may employ only a single homology clamp (e.g., some "hit-and-run"-type vectors, see, Bradley et al. *Bio/Technology* 10: 534 (1992), incorporated herein by reference).

The term "agent" is used herein to denote a chemical compound, a mixture of chemical compounds, a biological macromolecule, or an extract made from biological materials such as bacteria, plants, fungi, or animal (particularly mammalian) cells or tissues.

The term "cyclin inhibitor knockout phenotype" refers to a phenotypic characteristic present in cyclin inhibitor gene –/– animals (e.g., mice homozygous for functionally inactivated cyclin inhibitor alleles) and absent in wild-type animals of the same species, strain, sex, and age when raised under the same conditions. Examples include those described herein, for example: hyperplasia, overall hypertrophy, hypercellular and other phenotypic characteristics noted herein.

As used herein, "plant" refers to either a whole plant, a plant part, a plant cell, or a group of plant cells. The class of plants which can be used in the method of the invention is generally as broad as the class of higher plants amenable to transformation techniques, including bc monocotyledonous and dicotyledonous plants. It includes plants of a variety of ploidy levels, including polyploid, diploid and haploid.

An "isolated" polynucleotide or polypeptide is a polynucleotide or polypeptide which is substantially separated from other contaminants that naturally accompany it, e.g., protein, lipids, and other polynucleotide sequences. The term embraces polynucleotide sequences which have been removed or purified from their naturally-occurring environment or clone library, and include recombinant or cloned DNA isolates and chemically synthesized analogues or analogues biologically synthesized by heterologous systems.

Description of the Specific Embodiments

General Methods and Overview

The present invention provides compositions and methods for increasing the proportion of proliferating cells in a cell population by exposing the cell population to an inhibitor of p27 activity. The mediator can be directed to a nucleic acid molecule which encodes the p27 protein, i.e., the p27 gene or RNA transcripts thereof, or to the p27 protein itself, or subunits thereof. The inhibitor is provided to the cell population under conditions and in an amount sufficient to permitting progression of the cell cycle in the treated cells, thereby increasing the percentage of dividing cells in the cell population relative to an untreated cell population.

Modulating cell cycle regulation may be used to effect organism size and growth rate. Methods for modulating cell cycle include modulating the expression or activity of cyclin inhibitors, the expression or activity of cyclin activators, the expression of cyclin proteins and modulation of cyclin degradation, e.g., by regulating the ubiquitin pathway, e.g., human CDC34. Thus, in one aspect modulation of p27 affects the growth rate and size of an organism. In another aspect modulation of cyclin E is employed to affect organism size or growth rate. It may be advantageous to combine the modulation of various cell cycle regulators as described herein to amplify the effect on the rate of cell cycle progression and thus organism size or growth rate. For example, inhibition of p27 can be coupled with inhibition of other cyclin inhibitors, such as p21, p57, 16, p15, p18, and p19 to achieve increased growth rate and increased size.

p27 is a cellular protein having a molecular weight of about 27 kD that inhibits progression of the cell cycle through the Restriction point in early to mid-G1 phase. p27 acts by binding to and inhibiting the activation of cyclin E-Cdk2 and cyclin A-Cdk2 complexes. Characterization of the p27 protein and cloning and sequencing of the gene encoding the p27 protein are described in more detail in co-pending PCT application WO PCT/US95/07361, incorporated herein by reference.

Inhibitors of p27 are useful in the present invention to permit the activation of cyclin E-Cdk2 and cyclin A-Cdk2 complexes and the ensuing progression of the cell cycle through cell division. By maintaining p27 at sufficiently low levels repetitive cell cycling can be achieved. As the proportion of dividing cells in a given cell population increases, among other things the efficiency of transduction increases for viral vectors encoding desired gene products. Thus, the inhibitors are useful to overcome obstacles that have plagued gene therapy efforts. The inhibitors are particularly useful for increasing the population of dividing cells among hematopoietic stem cells, which represent a preferred target cell population for many gene therapy protocols.

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, cell culture, and transgene incorporation (e.g., electroporation, microinjection, lipofection). Generally enzymatic reactions, oligonucleotide synthesis, and purification steps are performed according to the manufacturer's specifications. The techniques and procedures are generally performed according to conventional methods in the art and various general references which are provided throughout this document. The procedures therein are believed to be well known in the art and are provided for the convenience of the reader. All the information contained therein is incorporated herein by reference.

Chimeric targeted mice are derived according to Hogan, et al., *Manipulating the Mouse Embryo: A Laboratory Manual*, Cold Spring Harbor Laboratory (1988) and *Teratocarcinomas and Embryonic Stem Cells: A Practical Approach*, E. J. Robertson, ed., IRL Press, Washington, D.C., (1987) which are incorporated herein by reference.

Embryonic stem cells are manipulated according to published procedures (*Teratocarcinomas and Embryonic Stem Cells: A Practical Approach*, E. J. Robertson, ed., IRL Press, Washington, D.C. (1987); Zjilstra et al., *Nature* 342:435-438 (1989); and Schwartzberg et al., *Science* 246:799-803 (1989), each of which is incorporated herein by reference).

Oligonucleotides can be synthesized on an Applied Bio Systems oligonucleotide synthesizer according to specifications provided by the manufacturer.

In general, the invention encompasses methods and polynucleotide constructs which are employed for generating nonhuman transgenic organisms having at least one endogenous cyclin inhibitor gene, such as p27, functionally inactivated and, in some embodiments, also harboring at least one heterologous cyclin inhibitor gene capable of expression.

Gene Targeting

Gene targeting, which is a method of using homologous recombination to modify a mammalian genome, can be used to introduce changes into cultured cells. By targeting a gene of interest in embryonic stem (ES) cells, these changes can be introduced into the germlines of laboratory animals to study the effects of the modifications on whole organisms, among other uses. The gene targeting procedure is accomplished by introducing into tissue culture cells a DNA targeting construct that has a segment homologous to a target locus and which also comprises an intended sequence modification (e.g., insertion, deletion, point mutation). The treated cells are then screened for accurate targeting to identify and isolate those which have been properly targeted. A common scheme to disrupt gene function by gene targeting in ES cells is to construct a targeting construct which is designed to undergo a homologous recombination with its chromosomal counterpart in the ES cell genome. The targeting constructs are typically arranged so that they insert additional sequences, such as a positive selection marker, into coding elements of the target gene, thereby functionally inactivating it. Targeting constructs usually are insertion-type or replacement-type constructs (Hasty et al. (1991) *Mol. Cell. Biol.* 11: 4509, incorporated herein by reference)

Targeting of Endogenous Cyclin Inhibitor Genes

The invention encompasses methods to produce nonhuman organisms that have endogenous cyclin inhibitor genes (i.e., at least one cyclin inhibitor locus) inactivated by gene targeting with a homologous recombination targeting construct. Typically, such nonhuman organisms have at least one functionally inactivated cyclin inhibitor gene. Typically, a cyclin inhibitor gene sequence is used as a basis for producing PCR primers that flank a region that will be used as a homology clamp in a targeting construct. The PCR primers are then used to amplify, by high fidelity PCR amplification (Mattila et al. (1991) *Nucleic Acids Res.* 19: 4967; Eckert, K. A. and Kunkel, T. A. (1991) *PCR Methods and Applications* 1: 17; U.S. Pat. No. 4,683,202, which are incorporated herein by reference), a genomic sequence from a genomic clone library or from a preparation of genomic DNA, preferably from the strain of nonhuman animal that is to be targeted with the targeting construct. The amplified DNA is then used as a homology clamp and/or targeting region. Thus, homology clamps for targeting essentially any cyclin inhibitor gene may be readily produced on the basis of nucleotide sequence information available in the art and/or by routine cloning. General principles regarding the construction of targeting constructs and selection methods are reviewed in Bradley et al. (1992) *Bio/Technology* 10: 534, incorporated herein by reference.

Targeting constructs can be transferred into pluripotent stem cells, such as murine embryonal stem cells, wherein the targeting constructs homologously recombine with a portion of an endogenous cyclin inhibitor gene locus and create mutation(s) (i.e., insertions, deletions, rearrangements, sequence replacements, and/or point mutations) which prevent the functional expression of the endogenous cyclin inhibitor gene.

A preferred method of the invention is to delete, by targeted homologous recombination, essential structural elements of an endogenous cyclin inhibitor gene. For example, a targeting construct can homologously recombine with an endogenous p27 gene and delete a portion spanning substantially all of one or more of the exons to create an exon-depleted allele, typically by inserting a replacement region lacking the corresponding exon(s). Transgenic animals homozygous for the exon-depleted allele (e.g., by breeding of heterozygotes to each other) produce cells which are essentially incapable of expressing a functional endogenous p27 molecule. Similarly, homologous gene targeting can be used, if desired, to functionally inactivate a cyclin inhibitor gene by deleting only a portion of an exon of an endogenous cyclin inhibitor gene.

Targeting constructs can also be used to delete essential regulatory elements of a cyclin inhibitor gene, such as promoters, enhancers, splice sites, polyadenylation sites, and other regulatory sequences, including sequences that occur upstream or downstream of the cyclin inhibitor structural gene but which participate in cyclin inhibitor gene expression. Deletion of regulatory elements is typically accomplished by inserting, by homologous double-crossover recombination, a replacement region lacking the corresponding regulatory element(s).

An alternative preferred method of the invention is to interrupt essential structural and/or regulatory elements of an endogenous cyclin inhibitor gene by targeted insertion of a polynucleotide sequence, and thereby functionally inactivate the endogenous cyclin inhibitor gene. For example, a targeting construct can homologously recombine with an endogenous p27 gene and insert a nonhomologous sequence, such as a neo expression cassette, into a structural element (e.g., an exon) and/or regulatory element (e.g., enhancer, promoter, splice site, polyadenylation site) to yield a targeted p27 allele having an insertional interruption. The inserted sequence can range in size from about 1 nucleotide (e.g., to produce a frameshift in an exon sequence) to several kilobases or more, as limited by efficiency of homologous gene targeting with targeting constructs having a long nonhomologous replacement region.

Targeting constructs of the invention can also be employed to replace a portion of an endogenous cyclin inhibitor gene with an exogenous sequence (i.e., a portion of a targeting transgene); for example, the first exon of a cyclin inhibitor gene may be replaced with a substantially identical portion that contains a nonsense or missense mutation.

Targeting Constructs

Several gene targeting techniques have been described, including but not limited to: co-electroporation, "hit-and-run", single-crossover integration, and double-crossover recombination (Bradley et al. (1992) *Bio/Technology* 10: 534, incorporated herein by reference). The invention can be practiced using essentially any applicable homologous gene targeting strategy known in the art. The configuration of a targeting construct depends upon the specific targeting technique chosen. For example, a targeting construct for single-crossover integration or "hit-and-run" targeting need only have a single homology clamp linked to the targeting region, whereas a double-crossover replacement-type targeting construct requires two homology clamps, one flanking each side of the replacement region.

For example and not limitation, an embodiment is a targeting construct comprising, in order: (1) a first homology clamp having a sequence substantially identical to a sequence within about 3 kilobases upstream (i.e., in the direction opposite to the translational reading frame of the cyclin inhibitor gene exons) of an exon of an endogenous cyclin inhibitor gene, (2) a replacement region comprising a positive selection cassette having a pgk promoter driving transcription of a neo gene, (3) a second homology clamp having a sequence substantially identical to a sequence within about 3 kilobases downstream of said exon of said endogenous cyclin inhibitor gene, and (4) a negative selection cassette, comprising a HSV tk promoter driving transcription of an HSV tk gene. Such a targeting construct is suitable for double-crossover replacement recombination which deletes a portion of the endogenous cyclin inhibitor locus spanning said exon and replaces it with the replacement region having the positive selection cassette. If the deleted exon is essential for expression of a functional cyclin inhibitor gene product, the resultant exon-depleted allele is functionally inactivated and is termed a null allele.

Targeting constructs of the invention comprise at least one homology clamp linked in polynucleotide linkage (i.e., by phosphodiester bonds) to a targeting region. A homology clamp has a sequence which substantially corresponds to, or is substantially complementary to, a predetermined endogenous cyclin inhibitor gene sequence of a nonhuman host organism, and may comprise sequences flanking the predetermined cyclin inhibitor gene.

Although no lower or upper size boundaries for recombinogenic homology clamps for gene targeting have been conclusively determined in the art, the best mode for homology clamps is believed to be in the range between about 50 basepairs and several tens of kilobases. Consequently, targeting constructs are generally at least about 50 to 100 nucleotides long, preferably at least about 250 to 500 nucleotides long, more preferably at least about 1000 to 2000 nucleotides long, or longer. Construct homology regions (homology clamps) are generally at least about 50 to 100 bases long, preferably at least about 100 to 500 bases long, and more preferably at least about 750 to 2000 bases long. It is believed that homology regions of about 7 to 8 kilobases in length are preferred, with one preferred embodiment having a first homology region, of about 7 kilobases flanking one side of a replacement region and a second homology region of about 1 kilobase flanking the other side of said replacement region. The length of homology (i.e., substantial identity) for a homology region may be selected at the discretion of the practitioner on the basis of the sequence composition and complexity of the predetermined endogenous cyclin inhibitor gene target sequence(s) and guidance provided in the art (Hasty et al. (1991) *Mol. Cell. Biol.* 11: 5586; Shulman et al. (1990) *Mol. Cell. Biol.* 10: 4466, which are incorporated herein by reference). The homology region which substantially corresponds to, or is substantially complementary to, a predetermined sequence (e.g., an exon sequence, an enhancer, a promoter, an intronic sequence, or a flanking sequence within about 3-20 kb of a cyclin inhibitor gene) serves as a template for homologous pairing and recombination with substantially identical endogenous cyclin inhibitor gene sequence(s). In targeting constructs, such homology regions typically flank the replacement region, which is a region of the targeting construct that is to undergo replacement with the targeted endogenous cyclin inhibitor gene sequence (Berinstein et al. *Mol. Cell. Biol.* 12: 360 (1992), which is incorporated herein by reference). Thus, a segment of the targeting construct flanked by homology regions can replace a segment of an endogenous cyclin inhibitor gene sequence by double-crossover homologous recombination. Homology regions and targeting regions are linked together in conventional linear polynucleotide linkage (5' to 3' phosphodiester backbone). Targeting constructs are generally double-stranded DNA molecules, most usually linear.

Without wishing to be bound by any particular theory of homologous recombination or gene conversion, it is believed that in such a double-crossover replacement recombination, a first homologous recombination (e.g., strand exchange, strand pairing, strand scission, strand ligation) between a first targeting construct homology region and a first endogenous cyclin inhibitor gene sequence is accompanied by a second homologous recombination between a second targeting construct homology region and a second endogenous cyclin inhibitor gene sequence, thereby resulting in the portion of the targeting construct that was located between the two homology regions replacing the portion of the endogenous cyclin inhibitor gene that was located between the first and second endogenous cyclin inhibitor gene sequences. For this reason, homology regions are generally used in the same orientation (i.e., the upstream direction is the same for each homology region of a transgene to avoid rearrangements). Double-crossover replacement recombination thus can be used to delete a portion of an endogenous cyclin inhibitor gene and concomitantly transfer a nonhomologous portion (e.g., a neo gene expression cassette) into the corresponding chromosomal location. Double-crossover recombination can also be used to add a nonhomologous portion into an endogenous cyclin inhibitor gene without deleting endogenous chromosomal portions. However, double-crossover recombination can also be employed simply to delete a portion of an endogenous gene sequence without transferring a nonhomologous portion into the endogenous cyclin inhibitor gene (see Jasin et al. (1988) *Genes Devel.* 2:1353). Upstream and/or downstream from the nonhomologous portion may be a gene which provides for identification of whether a double-crossover homologous recombination has occurred; such a gene is typically the HSV tk gene which may be used for negative selection.

The positive selection expression cassette encodes a selectable marker which affords a means for selecting cells which have integrated targeting transgene sequences spanning the positive selection expression cassette. The negative selection expression cassette encodes a selectable marker which affords a means for selecting cells which do not have an integrated copy of the negative selection expression cassette. Thus, by a combination positive-negative selection protocol, it is possible to select cells that have undergone homologous replacement recombination and incorporated the portion of the transgene between the homology regions (i.e., the replacement region) into a chromosomal location by selecting for the presence of the positive marker and for the absence of the negative marker. Selectable markers typically are also be used for hit-and-run targeting constructs and selection schemes (Valancius and Smithies, op.cit., incorporated herein by reference).

An expression cassette typically comprises a promoter which is operational in the targeted host cell (e.g., ES cell) linked to a structural sequence that encodes a protein or polypeptide that confers a selectable phenotype on the targeted host cell, and a polyadenylation signal. A promoter included in an expression cassette may be constitutive, cell type-specific, stage-specific, and/or modulatable (e.g., by hormones such as glucocorticoids; MMTV promoter), but is expressed prior to and/or during selection. An expression cassette can optionally include one or more enhancers, typically linked upstream of the promoter and within about 3-10 kilobases. However, when homologous recombination at the targeted endogenous site(s) places the nonhomologous sequence downstream of a functional endogenous promoter, it may be possible for the targeting construct replacement region to comprise only a structural sequence encoding the selectable marker, and rely upon the endogenous promoter to drive transcription (Doetschman et al. (1988) *Proc. Natl. Acad. Sci.* (*U.S.A.*) 85: 8583, incorporated herein by reference). Similarly, an endogenous enhancer located near the targeted endogenous site may be relied on to enhance transcription of transgene sequences in enhancerless transgene constructs. Preferred expression cassettes of the invention encode and express a selectable drug resistance marker and/or a HSV thymidine kinase enzyme. Suitable drug resistance genes include, for example: gpt (xanthine-guanine phosphoribosyltransferase), which can be selected for with mycophenolic acid; neo (neomycin phosphotransferase), which can be selected for with G418 or hygromycin; and DFHR (dihydrofolate reductase), which can be selected for with methotrexate (Mulligan and Berg (1981) *Proc. Natl. Acad. Sci.* (*U.S.A.*) 78: 2072; Southern and Berg (1982) *J. Mol. Appl. Genet.* 1: 327; which are incorporated herein by reference).

Selection for correctly targeted recombinants will generally employ at least positive selection, wherein a nonhomologous expression cassette encodes and expresses a functional protein (e.g., neo or gpt) that confers a selectable phenotype to targeted cells harboring the endogenously integrated expression cassette, so that, by addition of a selection agent (e.g., G418 or mycophenolic acid) such targeted cells have a growth or survival advantage over cells which do not have an integrated expression cassette.

It is preferable that selection for correctly targeted homologous recombinants also employ negative selection, so that cells bearing only nonhomologous integration of the transgene are selected against. Typically, such negative selection employs an expression cassette encoding the herpes simplex virus thymidine kinase gene (HSV tk) positioned in the transgene so that it should integrate only by nonhomologous recombination. Such positioning generally is accomplished by linking the HSV tk expression cassette (or other negative selection cassette) distal to the recombinogenic homology regions so that double-crossover replacement recombination of the homology regions transfers the positive selection expression cassette to a chromosomal location but does not transfer the HSV tk gene (or other negative selection cassette) to a chromosomal location. A nucleoside analog, gancyclovir, which is preferentially toxic to cells expressing HSV tk, can be used as the negative selection agent, as it selects for cells which do not have an integrated HSV tk expression cassette. FIAU may also be used as a selective agent to select for cells lacking HSV tk.

In order to reduce the background of cells having incorrectly integrated targeting construct sequences, a combination positive-negative selection scheme is typically used (Mansour et al. (1988) op.cit., incorporated herein by reference). Positive-negative selection involves the use of two active selection cassettes: (1) a positive one (e.g., the neo gene), that can be stably expressed following either random integration or homologous targeting, and (2) a negative one (e.g., the HSV tk gene), that can only be stably expressed following random integration, and cannot be expressed after correctly targeted double-crossover homologous recombination. By combining both positive and negative selection steps, host cells having the correctly targeted homologous recombination between the transgene and the endogenous cyclin inhibitor gene can be obtained.

Generally, targeting constructs of the invention preferably include: (1) a positive selection expression cassette flanked by two homology regions that are substantially identical to host cell endogenous cyclin inhibitor gene sequences, and (2) a distal negative selection expression cassette. However, targeting constructs which include only a positive selection expression cassette can also be used. Typically, a targeting construct will contain a positive selection expression cassette which includes a neo gene linked downstream (i.e., towards the carboxy-terminus of the encoded polypeptide in translational reading frame orientation) of a promoter such as the HSV tk promoter or the pgk promoter. More typically, the targeting transgene will also contain a negative selection expression cassette which includes an HSV tk gene linked downstream of a HSV tk promoter.

It is preferred that targeting constructs of the invention have homology regions that are highly homologous to the predetermined target endogenous DNA sequence(s), preferably isogenic (i.e., identical sequence). Isogenic or nearly isogenic sequences may be obtained by genomic cloning or high-fidelity PCR amplification of genomic DNA from the strain of nonhuman mammals which are the source of the ES cells used in the gene targeting procedure. Therefore, both homology region length and the degree of sequence homology can only be determined with reference to a particular predetermined sequence, but homology regions generally must be at least about 50 nucleotides long and must also substantially correspond or be substantially complementary to a predetermined endogenous target sequence. Preferably, a homology region is at least about 100 nucleotides long and is identical to or complementary to a predetermined target sequence in or flanking a cyclin inhibitor gene. If it is desired that correctly targeted homologous recombinants are generated at high efficiency, it is preferable that at least one homology region is isogenic (i.e., has exact sequence identity with the crossover target sequence(s) of the endogenous cyclin inhibitor gene), and is more preferred that isogenic homology regions flank the exogenous targeting construct sequence that is to replace the targeted endogenous cyclin inhibitor sequence.

Generally, any predetermined endogenous cyclin inhibitor locus can be altered by homologous recombination (which includes gene conversion) with a targeting transgene that has at least one homology region which substantially corresponds to or is substantially complementary to a predetermined endogenous cyclin inhibitor gene locus sequence in a mammalian cell having said predetermined endogenous cyclin inhibitor gene sequence. Typically, a targeting transgene comprises a portion having a sequence that is not present in the preselected endogenous targeted cyclin inhibitor sequence(s) (i.e., a nonhomologous portion) which may be as small as a single mismatched nucleotide or may span up to about several kilobases or more of nonhomologous sequence. Substitutions, additions, and deletions may be as small as 1 nucleotide or may range up to about 2 to 10 kilobases or more. Targeting transgenes can be used to inactivate one or more cyclin inhibitor genes in a cell, such as in a murine ES cell, and transgenic nonhuman organism harboring such inactivated genes may be produced.

Once the specific cyclin inhibitor gene(s) to be modified are selected, their sequences will be scanned for possible disruption sites. Plasmids are engineered to contain an appropriately sized construct replacement sequence with a deletion or insertion in the cyclin inhibitor gene of interest and at least one flanking homology region which substantially corresponds or is substantially complementary to an endogenous target DNA sequence. Typically two flanking homology regions are used, one on each side of the replacement region sequence. For example, but not to limit the invention, one homology region may be substantially identical to a sequence upstream (i.e., the direction towards the transcription start site(s) of the murine p27 first exon and a second homology region may be substantially identical to a sequence downstream of the murine p27 second exon.

A method of the invention is to transfer a targeting transgene into a pluripotent stem cell line which can be used to generate transgenic nonhuman animals following injection into a host blastocyst. In one embodiment of the invention is a p27 gene targeting construct containing both positive (e.g., neo) and, optionally, negative (e.g., HSV tk) selection expression cassettes. The p27 targeting transgene is transferred into mouse ES cells (e.g., by electroporation) under conditions suitable for the continued viability of the electroporated ES cells. The electroporated ES cells are cultured under selective conditions for positive selection (e.g., a selective concentration of G418), and optionally are cultured under selective conditions for negative selection (e.g., a selective concentration of gancyclovir or FIAU), either simultaneously or sequentially. Selected cells are then verified as having the correctly targeted transgene recombination by PCR analysis according to standard PCR or Southern blotting methods known in the art (U.S. Pat. No. 4,683,202; Erlich et al., *Science* 252: 1643 (1991), which are incorporated herein by reference). Correctly targeted ES cells are then transferred into suitable blastocyst hosts for generation of chimeric transgenic animals according to methods known in the art (Capecchi, M. (1989) op.cit., incorporated herein by reference).

Briefly, the invention involves regulation of cell cycle, for example the inactivation of a cyclin inhibitor gene, usually a p27 gene. Within one example a DNA construct that contains an altered, copy of a mouse cyclin inhibitor gene (e.g., a p27 gene) is introduced into the nuclei of embryonic stem cells. In a portion of the cells, the introduced DNA recombines with the endogenous copy of the mouse gene, replacing it with the altered copy. Cells containing the newly engineered genetic lesion are injected into a host mouse embryo, which is reimplanted into a recipient female. Some of these embryos develop into chimeric mice that possess germ cells derived from the mutant cell line. Therefore, by breeding the chimeric mice it is possible to obtain a new line of mice containing the introduced genetic lesion (reviewed by Capecchi, M. (1989) op.cit.).

In one example, to disrupt the murine $p27^{Kip1}$ gene, a targeting construct based on the design employed by Jaenisch and co-workers (Zjilstra, et al. (1989) op.cit.) for the successful disruption of the mouse β2-microglobulin gene can be used. The neomycin resistance gene (neo), from the plasmid pMC1NEO is inserted into the coding region of the target bcl-2 gene. The pMC1NEO insert uses a hybrid viral promoter/enhancer sequence to drive neo expression. This promoter is active in embryonic stem cells. Therefore, neo can be used as a selectable marker for integration of the knock-out construct. The HSV thymidine kinase (tk) gene is added to the end of the construct as a negative selection marker against random insertion events (Zjilstra, et al., op.cit.).

Vectors containing a targeting construct are typically grown in *E. coli* and then isolated using standard molecular biology methods, or may be synthesized as oligonucleotides. Direct targeted inactivation which does not require prokaryotic or eukaryotic vectors may also be done. Targeting transgenes can be transferred to host cells by any suitable technique, including microinjection, electroporation, lipofection, biolistics, calcium phosphate precipitation, and viral-based vectors, among others. Other methods used to transform mammalian cells include the use of Polybrene, protoplast fusion, and others (see, generally, Sambrook et al. Molecular Cloning: A Laboratory Manual, 2nd ed., 1989, Cold Spring Harbor Laboratory Press, Cold Spring Harbor, N.Y., which is incorporated herein by reference).

It is preferable to use a transfection technique with linearized transgenes containing only modified target gene sequence(s) and without vector sequences. The modified gene site is such that a homologous recombinant between the exogenous targeting construct and the endogenous DNA target sequence can be identified by using carefully chosen primers and PCR or by Southern blot analysis, followed by analysis to detect if PCR products or Southern blot bands specific to the desired targeted event are present (Erlich et al., (1991) op.cit.), which is incorporated herein by reference). Several studies have already used PCR to successfully identify the desired transfected cell lines (Zimmer and Gruss (1989) *Nature* 338: 150; Mouellic et al. (1990) *Proc. Natl. Acad. Sci.* (*U.S.A.*) 87: 4712; Shesely et al. (1991) *Proc. Natl. Acad. Sci. USA* 88: 4294, which are incorporated herein by reference). This approach is very effective when the number of cells receiving exogenous targeting transgene(s) is high (i.e., with electroporation or with liposomes) and the treated cell populations are allowed to expand (Capecchi, M. (1989) op.cit., incorporated herein by reference).

For making transgenic non-human organisms (which include homologously targeted non-human animals), embryonal stem cells (ES cells) are preferred. Murine ES cells, such as AB-1 line grown on mitotically inactive SNL76/7 cell feeder layers (McMahon and Bradley, *Cell* 62:1073-1085 (1990)) essentially as described (Robertson, E. J. (1987) in *Teratocarcinomas and Embryonic Stem Cells: A Practical Approach*. E. J. Robertson, ed. (Oxford: IRL Press), p. 71-112) may be used for homologous gene targeting. Other suitable ES lines include, but are not limited to, the E14 line (Hooper et al. (1987) *Nature* 326: 292-295), the D3 line (Doetschman et al. (1985) *J. Embryol. Exp. Morph.* 87: 27-45), and the CCE line (Robertson et al. (1986) *Nature* 323: 445-448). The success of generating a mouse line from ES cells bearing a specific targeted mutation depends on the pluripotence of the ES cells (i.e., their ability, once injected into a host blastocyst, to participate in embryogenesis and contribute to the germ cells of the resulting animal). The blastocysts containing the injected ES cells are allowed to develop in the uteri of pseudopregnant nonhuman females and are born as chimeric mice. The resultant transgenic mice are chimeric for cells having inactivated endogenous cyclin inhibitor loci and are backcrossed and screened for the presence of the correctly targeted transgene(s) by PCR or Southern blot analysis on tail biopsy DNA of offspring so as to identify transgenic mice heterozygous for the inactivated cyclin inhibitor locus/loci. By performing the appropriate crosses, it is possible to produce a transgenic nonhuman animal homozygous for multiple functionally inactivated cyclin inhibitor loci, and optionally also for a transgene encoding a heterologous cyclin inhibitor protein. Such transgenic animals are substantially incapable of making an endogenous cyclin inhibitor gene product. For these reasons, such transgenic animals are satisfactory hosts for introduction of transgenes encoding heterologous cyclin inhibitor proteins, such as, for example, a transgene encoding human p27 integrated into a mouse genome.

Inactivation of an endogenous mouse cyclin inhibitor locus is achieved by targeted disruption of the appropriate gene by homologous recombination in mouse embryonic stem cells. For inactivation, any targeting construct that produces a genetic alteration in the target cyclin inhibitor gene locus resulting in the prevention of effective expression of a functional gene product of that locus may be employed. If only regulatory elements are targeted, some low-level expression of the targeted gene may occur (i.e., the targeted allele is "leaky"), however the level of expression may be sufficiently low that the leaky targeted allele is functionally inactivated.

Knockout Animals

In one embodiment of the invention, an endogenous cyclin inhibitor gene in a nonhuman host is functionally inactivated by homologous recombination with a targeting construct that does not comprise a heterologous cyclin inhibitor gene segment. In this embodiment, a portion of the targeting construct integrates into an essential structural or regulatory element of the endogenous cyclin inhibitor gene locus, thereby functionally inactivating it to generate a null allele. Typically, null alleles are produced by integrating a nonhomologous sequence encoding a selectable marker (e.g., a neo gene expression cassette) into an essential structural and/or regulatory sequence of a cyclin inhibitor gene by homologous recombination of the targeting construct homology clamps with endogenous cyclin inhibitor gene sequences, although other strategies (see, infra) may be employed.

Most usually, a targeting construct is transferred by electroporation or microinjection into a totipotent embryonal stem (ES) cell line, such as the murine AB-1 or CCE lines. The targeting construct homologously recombines with endogenous sequences in or flanking a cyclin inhibitor gene locus and functionally inactivates at least one allele of the cyclin inhibitor gene. Typically, homologous recombination of the targeting construct with endogenous cyclin inhibitor locus sequences results in integration of a nonhomologous sequence encoding and expressing a selectable marker, such as neo, usually in the form of a positive selection cassette (infra). The functionally inactivated allele is termed a cyclin inhibitor null allele. ES cells having at least one cyclin inhibitor null allele are selected for by propagating the cells in a medium that permits the preferential propagation of cells expressing the selectable marker. Selected ES cells are examined by PCR analysis and/or Southern blot analysis to verify the presence of a correctly targeted cyclin inhibitor allele. Breeding of nonhuman animals which are heterozygous for a null allele may be performed to produce nonhuman animals homozygous for said null allele, so-called "knockout" animals (Donehower et al. (1992) Nature 256: 215; Science 256: 1392, incorporated herein by reference). Alternatively, ES cells homozygous for a null allele having an integrated selectable marker can be produced in culture by selection in a medium containing high levels of the selection agent (e.g., G418 or hygromycin). Heterozygosity and/or homozygosity for a correctly targeted null allele can be verified with PCR analysis and/or Southern blot analysis of DNA isolated from an aliquot of a selected ES cell clone and/or from tail biopsies.

If desired, a transgene encoding a heterologous cyclin inhibitor protein can be transferred into a nonhuman host having a cyclin inhibitor null allele, preferably into a nonhuman ES cell that is homozygous for the null allele. It is generally advantageous that the transgene comprises a promoter and enhancer which drive expression of structural sequences encoding a functional heterologous cyclin inhibitor gene product. Thus, for example and not limitation, a knockout mouse homozygous for null alleles at the $p27^{Kip1}$ locus is preferably a host for a transgene which encodes and expresses a functional human p27 protein.

Nonhuman animals comprising germline copies of a functionally inactivated cyclin inhibitor gene, such as a structurally disrupted p27 gene, are produced. Preferably the knockout animals are homozygous for the functionally inactivated cyclin inhibitor gene.

The knockout organisms can be used with methods for identifying agents that are cyclin inhibitor gene product mimetics (i.e., have CDK inhibition activity; can replace gene function in a cyclin inhibitor gene knockout background) or cyclin inhibitor agonists (i.e., enhance function of endogenous p27 in a hemizygote) or cyclin inhibitor antagonists (i.e., inhibit residual p27 function in a hemizygote). Transgenic nonhuman animals lacking functional cyclin inhibitor alleles define whole-animal cyclin inhibitor knockout phenotypes. Agents that can reverse a whole-animal cyclin inhibitor knockout phenotype (i.e., induce a reversion to phenotypic characteristics of normal, non-knockout animals) when administered to a cyclin inhibitor knockout animal are identified as cyclin inhibitor mimetics. Agents that can reverse a whole-animal cyclin inhibitor knockout phenotype (i.e., induce a reversion to phenotypic characteristics of normal, non-knockout animals) when administered to an animal which comprises reduced cyclin inhibitor function (e.g., partial cyclin inhibitor knockout or reduced cyclin inhibitor expression animals; such as by hemizygosity or partial antisense suppression) are identified as cyclin inhibitor agonists. Agents that can induce a whole-animal cyclin inhibitor knockout phenotype (i.e., induce phenotypic characteristics of cyclin inhibitor-knockout animals) when administered to normal, non-knockout animals are identified as cyclin inhibitor antagonists. These types of agents can be used to control cell proliferation for morphologic growth regulation to control animal size and body characteristics, to treat or prevent diseases of abnormal cell proliferation (e.g., neoplasia, hyperplasia, inflammation, and the like), as commercial laboratory reagents which can be sold to the biotechnology industry and research institutions (akin to patented restriction endonucleases, PCR reagents, and the like), among other uses related to the control of cell proliferation.

Nonhuman animals comprising knockout alleles of cyclin inhibitor genes, such as p27, can be used commercially for toxicological evaluation of test agents on the knockout animals which represent animals compromised in cell proliferation control pathways. The cyclin inhibitor gene knockouts of the present invention result in animals that have enhanced cell proliferation and can be predisposed to developing cell proliferation control diseases as compared to normal (non-knockout) animals. Such gene knockout animals have many uses, including but not limited to identifying compounds that effect or affect cell proliferation control; in one variation, the agents are thereby identified as toxicological hazards. The knockout animals can also be used to develop agents that modulate cell proliferation; such agents can serve as therapeutic agents to treat cell proliferation-related diseases, such as neoplasia or hyperplasia (e.g., BPH). The knockout animals of the invention can also serve as disease models for investigating cell proliferation-related pathological conditions (e.g., ALS, Alzheimer's disease, AIDS, and the like).

Suppressing Expression of Endogenous Cyclin Inhibitor Loci

Suppression is an alternative method for preventing the expression of an endogenous cyclin inhibitor locus. Suppression of endogenous cyclin inhibitor genes may be accomplished with antisense RNA produced from one or more integrated transgenes, by antisense oligonucleotides, and/or by expression of intracellular polypeptides which inactivate the cyclin inhibitor gene product.

Antisense Polynucleotides

Antisense RNA transgenes can be employed to partially or totally knock-out expression of specific genes (Pepin et al. (1991) Nature 355: 725; Helene., C. and Toulme, J. (1990) Biochimica Biophys. Acta 1049: 99; Stout, J. and Caskey, T. (1990) Somat. Cell Mol. Genet. 16: 369; Munir et al. (1990) Somat. Cell Mol. Genet. 16: 383, each of which is incorporated herein by reference).

"Antisense polynucleotides" are polynucleotides that: (1) are complementary to all or part of a reference sequence, such as a sequence of an endogenous cyclin inhibitor gene region, and (2) which specifically hybridize to a complementary target sequence, such as a chromosomal gene locus or a mRNA. Such complementary antisense polynucleotides may include nucleotide substitutions, additions, deletions, or transpositions, so long as specific hybridization to the relevant target sequence is retained as a functional property of the polynucleotide. Complementary antisense polynucleotides include soluble antisense RNA or DNA oligonucleotides which can hybridize specifically to individual mRNA species and prevent transcription and/or RNA processing of the mRNA species and/or translation of the encoded polypeptide (Ching et al., *Proc. Natl. Acad. Sci. U.S.A.* 86:10006-10010 (1989); Broder et al., *Ann. Int. Med.* 113:604-618 (1990); Loreau et al., *FEBS Letters* 274:53-56 (1990); Holcenberg et al., WO91/11535; U.S. Ser. No. 07/530,165 ("New human CRIPTO gene"); WO91/09865; WO91/04753; WO90/13641; and EP 386563, each of which is incorporated herein by reference). An antisense sequence is a polynucleotide sequence that is complementary to at least one cyclin inhibitor gene sequence of at least about 11 contiguous nucleotides in length, typically at least 20 to 30 nucleotides in length, and preferably more than about 30 nucleotides in length. However, in some embodiments, antisense sequences may have substitutions, additions, or deletions as compared to the complementary cyclin inhibitor gene sequence, so long as specific hybridization is retained as a property of the antisense polynucleotide. Generally, an antisense sequence is complementary to an endogenous cyclin inhibitor gene sequence that encodes, or has the potential to encode after DNA rearrangement, an cyclin inhibitor gene product. In some cases, sense sequences corresponding to an cyclin inhibitor gene sequence may function to suppress expression, particularly by interfering with transcription.

The antisense polynucleotides therefore inhibit production of the encoded polypeptide(s). In this regard, antisense polynucleotides that inhibit transcription and/or translation of one or more endogenous cyclin inhibitor loci can alter the capacity and/or specificity of a non-human organism to produce cyclin inhibitor gene products encoded by endogenous cyclin inhibitor loci, and thereby exhibit an altered cell proliferation phenotype.

Antisense polynucleotides may be produced from a heterologous expression cassette in a transfectant cell or transgenic cell, such as a transgenic pluripotent hematopoietic stem cell used to reconstitute all or part of the stem cell population of an individual, or as a germline copy integrated (or otherwise episomally replicated) in the genome of transgenic nonhuman animal. Alternatively, the antisense polynucleotides may comprise soluble oligonucleotides that are administered to the external milieu, either in culture medium in vitro or in the circulatory system or interstitial fluid in vivo. Soluble antisense polynucleotides present in the external milieu have been shown to gain access to the cytoplasm and inhibit translation of specific mRNA species. In some embodiments the antisense polynucleotides comprise methylphosphonate moieties, alternatively phosphorothiolates or O-methylribonucleotides may be used, and chimeric oligonucleotides may also be used (Dagle et al. (1990) *Nucleic Acids Res.* 18: 4751). For some applications, antisense oligonucleotides may comprise polyamide nucleic acids (Nielsen et al. (1991) *Science* 254: 1497). For general methods relating to antisense polynucleotides, see *Antisense RNA and DNA*, (1988), D. A. Melton, Ed., Cold Spring Harbor Laboratory, Cold Spring Harbor, N.Y.).

Whether as soluble antisense oligonucleotides or as antisense RNA transcribed from an antisense transgene, the antisense polynucleotides of this invention are selected so as to hybridize preferentially to endogenous cyclin inhibitor gene sequences at physiological conditions in vivo.

Polynucleotides of this invention may serve as antisense vectors or sense suppression constructs for introduction into a plant genome or as integrated into a plant genome at a position other than a naturally-occurring cyclin inhibitor locus or in place of a naturally-occurring cyclin inhibitor locus (e.g., by replacement homologous recombination).

Cyclin Inhibitor Transgenes

Whereas expression of an endogenous cyclin inhibitor gene and/or the encoded protein can be inhibited by antisense suppression and/or related methods, the invention also provides polynucleotides which encode a cyclin inhibitor gene product or variant thereof and which, when introduced into a suitable animal or plant genome, are expressed as a functional cyclin inhibitor protein in the host animal or plant.

For expression or overexpression of a cyclin inhibitor gene product, a polynucleotide encoding a cyclin inhibitor polypeptide having detectable CDK inhibition activity (e.g., p27) is introduced into a suitable animal or plant genome in a form suitable for expression as desired. Typically, the cyclin inhibitor encoding polynucleotide is operably linked to a transcriptional regulatory sequence (e.g., promoter, optional enhancer, polyadenylation sequence, etc.) capable of driving transcription of the cyclin inhibitor encoding sequence such that a translatable mRNA is ultimately produced (i.e., RNA splicing of the primary transcript can be required in some embodiments). In a variation, a cyclin inhibitor encoding polynucleotide can be targeted, by homologous recombination gene targeting, into a position adjacent to an operable endogenous promoter in a genome, such that the resultant endogenous chromosomal locus comprises a cyclin inhibitor encoding polynucleotide in operable linkage to an endogenous promoter, and optionally an endogenous polyadenylation sequence and transcription termination sequence. In an embodiment, the cyclin inhibitor encoding polynucleotide can encode a full-length cyclin inhibitor protein, although truncated variants or other deletion, addition, or substitution variants can be used. In an embodiment, the cyclin inhibitor encoding polynucleotide encodes a fusion protein comprising a full-length cyclin inhibitor protein or active portion thereof in polypeptide linkage to a fusion partner sequence, such as the sequence of a naturally-occurring gene other than the cyclin inhibitor gene.

A cyclin inhibitor encoding polynucleotide typically in operable linkage to a transcriptional regulatory sequence (e.g., promoter) and capable of expression is introduced into a genome of a suitable animal (e.g., nonhuman mammal, fish, reptile, bird) or plant variety (e.g., pepper, tomato, tomatillo, etc.). Individuals exhibiting a desired phenotype characterized by expression of the cyclin inhibitor protein encoded by the introduced polynucleotide are selected on the basis of a desired phenotype which is determined, such as by enzyme assay, visual inspection, pathological condition, and the like.

Thus, the invention provides a means of expressing a cyclin inhibitor gene (e.g., p27) under control of a heterologous promoter for any desired purpose. It can be advantageous to use cyclin inhibitor gene expression constructs to produce expression of a hyperphysiological level of a cyclin inhibitor gene product in a cell, cell type, tissue, organ, or organism. For example, such animals and plants exhibit enhanced levels of cyclin inhibitor activity can possess advantageous properties, such as decreased size and cellularity, and the like.

Constructs and Introduction

In considering the expected temporal stage of expression of the introduced gene, relevant factors include the type of promoter, the temporal pattern of the promoter, and the operation of the promoter in view of its position within the genome. A promoter which is expressed concurrently with or prior to the normal activation of the homologous endogenous sequence is preferred. A constitutive promoter is often preferred, such as the CMV promoter. This promoter is constitutive because its operation is relatively independent of the developmental stage of the cell in which it is contained. A regulated promoter is also suitable. This control may be either temporal with respect to the developmental stage of the cell, or based upon differential expression by different parts or organs of the organism.

Another way to regulate the time of expression of the introduced sequence is by linking the introduced sequence to an inducible promoter that can be activated by causing the organism (or part thereof) to be exposed to an inducing agent (e.g., a steroid hormone in the case of a steroid-responsive promoter/enhancer), chemical, UV or other light source, or another activating treatment. It may also be desirable to suppress a gene in one part of an organism only using promoters that direct transcription in one part or organ of an organism only (i.e., a fruiting body of a plant).

As referred to above, the operation of a promoter may vary depending on its location in the genome. Thus, a regulated promoter may operate differently from how it does in its normal location, e.g., it may become fully or partially constitutive.

It is preferred to have the DNA sequence linked to and situated at a distance from the promoter corresponding to the distance at which the promoter is normally most effective so as to ensure sufficient transcriptional activity. This distance should be within about 1000 nucleotides, preferably within about 500 nucleotides and more preferably within about 300 nucleotides of the translation initiation codon.

At the 3' end of the coding sequence, operably linked segments may also be included. Thus, it would be optimum to have a 3' untranslated region containing the polyadenylation site and any relevant transcription termination sites. A 3' sequence of less than about 1000 nucleotides is sufficient, about 500 preferred and about 300, or the length of the 3' untranslated tail of the endogenous sequence is more preferred.

If the introduced cyclin inhibitor gene is an intact gene or cDNA a fraction of independent transgenotes, depending on the gene, may carry the introduced gene in locations that result in abnormal expression, i.e., expression at abnormal times in development. If the introduced gene is a chimeric gene (meaning that one or more elements, such as a promoter, from another gene has been substituted for a component of the intact gene or added to the intact gene, including coding sequences fused to upstream and downstream sequences necessary or beneficial for expression) and is driven by a constitutive (fully or partially) promoter, then abnormal levels and times of expression will be achieved in a large fraction of transgenotes. If the introduced gene is a chimeric gene and is driven by a developmentally regulated promoter, depending on the promoter, some fraction of transgenotes will show abnormal levels and times of expression of the introduced gene. The strength of the promoter or other cis element can be the same, lower, or higher than the coding sequence's usual promoter. The timing in development can be earlier or the same.

Polynucleotides encoding full-length cyclin inhibitor gene products or fragments or analogs thereof, may include sequences that facilitate transcription (expression sequences) and translation of the coding sequences, such that the encoded polypeptide product is produced. Construction of such polynucleotides is well known in the art and is described further in Maniatis et al., *Molecular Cloning: A Laboratory Manual*, 2nd Ed. (1989), Cold Spring Harbor, N.Y. For example, but not for limitation, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector. A typical eukaryotic expression cassette will include a polynucleotide sequence encoding a cyclin inhibitor polypeptide linked downstream (i.e., in translational reading frame orientation; polynucleotide linkage) of a promoter such as the HSV tk promoter or the pgk (phosphoglycerate kinase) promoter, optionally linked to an enhancer and a downstream polyadenylation site (e.g., an SV40 large T Ag poly A addition site).

Additionally, a cyclin inhibitor gene or cDNA may be used to construct transgenes for expressing cyclin inhibitor polypeptides at high levels and/or under the transcriptional control of transcription control sequences which do not naturally occur adjacent to the cyclin inhibitor gene. For example but not limitation, a constitutive promoter (e.g., a HSV-tk or pgk promoter) or a cell-lineage specific transcriptional regulatory sequence (e.g., a CD4 or CD8 gene promoter/enhancer) may be operably linked to a cyclin inhibitor-encoding polynucleotide sequence to form a transgene (typically in combination with a selectable marker such as a neo gene expression cassette). Such transgenes can be introduced into cells (e.g., ES cells, hematopoietic stem cells) and transgenic cells and transgenic nonhuman animals may be obtained according to conventional methods.

The likelihood of obtaining a desirable transgenote will depend upon the number of transgenotes screened and the efficiency of actual transformation and expression of the foreign nucleic acid sequence. Typically, at least about 25 to 50 transgenotes will be screened, but 100 to 500 or more may need to be screened before the described effect is seen.

Suppression and Expression Transgenes in Plants

In general, a transcribable cyclin inhibitor polynucleotide sequence or its reverse complement contain an operably linked promoter capable of functioning in the cell into which the polynucleotide is to be transferred. The transcribable cyclin inhibitor polynucleotide sequence is at least 25 nucleotides long, more usually at least 50-100 nucleotides long, frequently at least 100-250 nucleotides long, often at least 500 nucleotides long or longer, up to the length of the complete endogenous gene (spanning promoter through transcription termination sequence/polyadenylation site). The transcribable cyclin inhibitor sequence is positioned relative to the promoter such that a RNA transcript of the transcribable sequence is the same or reverse complement polarity as the mRNA transcript of the endogenous gene (i.e., sense or antisense orientation). The suppression polynucleotide may be part of a larger polynucleotide, such as a transgene having a selectable marker to identify cells having integrated the transgene, or a homologous recombination construct having selectable marker(s) and homology regions for targeting the suppression polynucleotide to a predetermined location in the genome of cells. Suppression polynucleotides may be in the form of a heterologous expression cassette in a transfectant cell or transgenic cell. Often, the suppression polynucleotide is obtained as a vector produced with DNA isolated from a cloned copy (or portion thereof) of the target endogenous gene to be suppressed. The suppression polynucleotide sequence is usually isolated as part of a genomic gene clone, although in some embodiments a cDNA clone (or portion thereof) of the target gene to be suppressed can be employed (for general cDNA methods see, Goodspeed et al. (1989) *Gene* 76: 1; Dunn et al. (1989) *J. Biol. Chem.* 264: 13057).

Vectors containing a suppression polynucleotide are typically grown in *E. coli* and then isolated using standard molecular biology methods, or may be synthesized as oligonucleotides. Direct polynucleotide synthesis and ligation (if necessary) which does not require prokaryotic or eukaryotic vectors may also be done. Polynucleotides (and transgenes comprising such) can be transferred to host cells by any suitable technique, including microinjection, electroporation, lipofection, biolistics, calcium phosphate precipitation, and viral-based vectors, among others (e.g., U.S. Pat. Nos. 5,442,052, 5,354,854, 5,278,057, 5,262,316, 5,137,817, and 4,962,028, incorporated herein by reference). A preferred method of introducing the nucleic acid segments into plant cells is to infect a plant cell, an explant, a meristem or a seed with *Agrobacterium tumefaciens* transformed with the segment. Under appropriate conditions known in the art, the transformed plant cells are grown to form shoots, roots, and develop further into plants. The nucleic acid segments can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al., (1984) "Inheritance of Functional Foreign Genes in Plants," *Science*, 233:496-498; Fraley et al., (1983) *Proc. Natl. Acad. Sci. USA* 80:4803). One *Agrobacterium* method is in planta *Agrobacterium*-mediated gene transfer by infiltration, e.g., of adult *Arabidopsis thaliana* plants; Bechtold et al. (1993) *C. R. Acad. Sci. Life Sciences* 316: 1194 et seq., incorporated herein by reference).

All plant cells which can be transformed by *Agrobacterium* and whole plants regenerated from the transformed cells can also be transformed according to the invention so as to produce transformed whole plants which contain the transferred foreign nucleic acid sequence.

Plant cells can be transformed with *Agrobacterium* in various ways, including: co-cultivation of *Agrobacterium* with cultured isolated protoplasts, transformation of cells or tissues with *Agrobacterium*, or transformation of seeds, apices or meristems with *Agrobacterium*.

A preferred system is the binary system in which two plasmids are needed: a T-DNA containing plasmid and a vir plasmid. Any one of a number of T-DNA containing plasmids can be used, the only requirement is that one be able to select independently for each of the two plasmids.

After transformation of the plant cell or plant, those plant cells or plants transformed by the Ti plasmid so that the desired DNA segment is integrated can be selected by an appropriate phenotypic marker. These phenotypic markers include, but are not limited to, antibiotic resistance, herbicide resistance or visual observation. Other phenotypic markers are known in the art and may be used in this invention.

If naked nucleic acid introduction methods are chosen, then the vector need be no more than the minimal nucleic acid sequences necessary to confer the desired traits, without the need for additional other sequences. Thus, the possible vectors include the Ti plasmid vectors, shuttle vectors designed merely to maximally yield high numbers of copies, episomal vectors containing minimal sequences necessary for ultimate replication once transformation has occurred, transposon vectors, homologous recombination vectors, mini-chromosome vectors, and viral vectors, including the possibility of RNA forms of the gene sequences. The selection of vectors and methods to construct them are commonly known to persons of ordinary skill in the art and are described in general technical references (Methods in Enzymology, supra).

However, any additional attached vector sequences which will confer resistance to degradation of the nucleic acid fragment to be introduced, which assists in the process of genomic integration or provides a means to easily select for those cells or plants which are actually, in fact, transformed are advantageous and greatly decrease the difficulty of selecting useable transgenotes.

All transformable plants from which whole regenerated plants can be generated can be used in the present invention. Monocots may be transformed with *Agrobacterium* by electroporation (Fromm et al. [1986] *Nature* 319:791-793; Rhodes et al. *Science* [1988] 240: 204-207); by direct gene transfer (Baker et al. [1985] *Plant Genetics* 201-211); by using pollen-mediated vectors (EP 0 270 356); and by injection of DNA into floral tillers (de la Pena et al. [1987], *Nature* 325:274-276)

Cyclin Inhibitors p27 inhibitors that permit the activation of cyclin E-Cdk2 and/or cyclin A-Cdk2 complexes can be identified in a variety of screening assay formats. Inhibitors of p27-mediated activation of cyclin E-Cdk2 and/or cyclin A-Cdk2 in the presence of p27 can be screened, for example, using an assay in which test substances are exposed to suitable amounts of p27 protein, cyclin E and or cyclin A, and Cdk2 under conditions that permit the formation of active cyclin E- or cyclin A-Cdk2 complexes in the absence of p27. The active cyclin E- and/or cyclin A-Cdk2 complexes formed are then quantitated and compared to the active complexes formed in the absence of the test substance.

Substances which can serve as p27 inhibitors include, but are not limited to, compounds capable of inhibiting the p27-mediated inhibition of cyclin E-Cdk2 complex activation, compounds that specifically inhibit the interaction between p27 and cyclin E-Cdk2 complexes and/or between p27 and cyclin A-Cdk2 complexes, but not the site-specific phosphorylation of the Cdk2 moiety of the cyclin-Cdk2 complex in the absence of p27, compounds that degrade or inactivate the p27 protein, and compounds that interfere with the expression of p27 protein. Such agents may include chemical compound inhibitors of p27, protein or peptide p27 antagonists, and molecules that inhibit the expression of p27 such as triplex forming oligonucleotides, antisense oligonucleotides, ribozymes, etc.

For use as p27 inhibitors in the present invention to mediate cell cycle progression, the triplex forming oligonucleotides are p27 sequence-specific DNA binding drugs that interfere with p27 transcription. Triplex-forming oligonucleotides are generally described in Maher, *Bioessays* 14: 807-815 (1992); Gee et al., *Gene* 149: 109-114 (1994); Noonberg et al., *Gene* 149: 123-126 (1994); Song et al., *Ann. NY Acad. Sci.* 761: 97-108 (1995); Westin et al., *Nuc. Acids. Res.* 23: 2184-2191 (1995); and Wand and Glazer, *J. Biol. Chem.* 207: 22595-22901 (1995). These oligonucleotides form triple helical complexes, under physiological conditions, on double-stranded DNA selectively inhibiting p27 transcription by physically blocking RNA polymerase or transcription factor access to the p27 DNA template. See also, e.g., WO 95/25818; WO 95/20404; WO 94/15616; WO 94/04550; and WO 93/09788, each of which is incorporated herein by reference. The triplex forming oligonucleotides targeted to the p27 gene may contain either a nucleotide or non-nucleotide tail to enhance the inhibition of transcription factor binding.

Antisense oligonucleotides that interfere with the expression of p27 and permit progression of the cell cycle, as exemplified in the Examples described hereinbelow, are particularly useful in the present invention. p27 antisense inhibitors are identified using methods, e.g., as described in detail in the Examples. The use of antisense oligonucleotides and their applications are described generally in, for example, Mol and Van der Krul, eds., *Antisense Nucleic Acids and Proteins Fundamentals and Applications*, New York, N.Y., 1992, which is incorporated by reference herein in its entirety. Suitable antisense oligonucleotides are at least 11 nucleotide in length and up to and including the upstream untranslated and associated coding sequences of p27. As will be evident to one skilled in the art, the optimal length of antisense oligonucleotides is dependent on the strength of the interaction between the antisense oligonucleotides and their complementary sequence on the mRNA, the temperature and ionic environment translation takes place, the base sequence of the antisense oligonucleotide, and the presence of secondary and tertiary structure in the mRNA and/or in the antisense oligonucleotide. Suitable target sequences for antisense oligonucleotides include intron-exon junctions (to prevent proper splicing), regions in which DNA/RNA hybrids will prevent transport of mRNA from the nucleus to the cytoplasm, initiation factor binding sites, ribosome binding sites, and sites that interfere with ribosome progression. A particularly preferred target region for antisense oligonucleotide is the 5' untranslated region of the p27 gene.

Antisense polynucleotides targeted to the p27 gene are prepared by inserting a DNA molecule containing the target DNA sequence into a suitable expression vector such that the DNA molecule is inserted downstream of a promoter in a reverse orientation as compared to the gene itself. The expression vector may then be transduced, transformed or transfected into a suitable cell resulting in the expression of antisense polynucleotides. Alternatively, antisense oligonucleotides may be synthesized using standard manual or automated synthesis techniques. Synthesized oligonucleotides may be introduced into suitable cells by a variety of means including electroporation (e.g., as described in Yang et al., *Nucl. Acids. Res.* 23:2803-2810 (1995)), calcium phosphate precipitation, microinjection, poly-L-ornithine/DMSO (Dong et al., *Nucl. Acids. Res.* 21:771-772 (1993)). The selection of a suitable antisense oligonucleotide administration method will be evident to one skilled in the art. With respect to synthesized oligonucleotides, the stability of antisense oligonucleotides-mRNA hybrids may be increased by the addition of stabilizing agents to the oligonucleotide. Stabilizing agents include intercalating agents that are covalently attached to either or both ends of the oligonucleotide. Oligonucleotides may be made resistant to nucleases by, for example, modifications to the phosphodiester backbone by the introduction of phosphotriesters, phosphonates, phosphorothioates, phosphoroselenoates, phosphoramidates or phosphorodithioates. Oligonucleotides may also be made nuclease resistant by the synthesis of the oligonucleotides with alpha-anomers of the deoxyribonucleotides, as generally described in Mol and Van der Krul, supra.

For oligonucleotide-based inhibitors, the choice of a suitable sequence will be guided by, for example, the type of inhibitor (i.e., triplex forming oligonucleotide or antisense oligonucleotide) and the species to be treated. It may be preferable to choose sequences that are conserved between species to permit use in readily available animal models. As shown in more detail below, antisense oligonucleotides to sequences within p27 that are conserved between mouse and human were chosen for use in the mouse model. Such sequences may then be used in human cells without reformulation.

The present invention also provides compositions and methods for inhibiting p27 and thereby permitting cell cycle progression using ribozymes. The ribozymes can be administered in a variety of ways, including by gene therapy targeted to a desired cell. A ribozyme of the invention targets the RNA transcripts of the p27 gene. Each ribozyme molecule contains a catalytically active segment capable of cleaving the p27 RNA, and further comprises flanking sequences having a nucleotide sequence complementary to portions of the targeted RNA. The flanking sequences serve to anneal the ribozyme to the RNA in a site-specific manner. Absolute complementarity of the flanking sequences to the target p27 sequence is not necessary, however, as only an amount of complementarity sufficient to form a duplex with the target RNA and to allow the catalytically active segment of the ribozyme to cleave at the target sites is necessary. Thus, only sufficient complementarity to permit the ribozyme to be hybridizable with the target RNA is required.

As used herein, the term "ribozyme" means an RNA molecule having an enzymatic activity that is able to cleave or splice other separate RNA molecules in a nucleotide base sequence specific manner. By reference to catalytic or enzymatic RNA molecule is meant an RNA molecule which has complementarity in a substrate binding region to a specific p27 RNA target, and also has enzymatic activity that is active to cleave and/or splice RNA in that target, thereby altering the target molecule. In preferred embodiments of the present invention the enzymatic RNA molecule is formed in a hammerhead motif, but the ribozyme may also be formed in the motif of a hairpin, hepatitis delta virus, group I intron or RNAse P RNA (in association with an RNA guide sequence). Examples of hammerhead motifs are described by Rossi et al., *AIDS Res. Hum. Retrovir.* 8: 183 (1992), hairpin motifs are described by Hampel et al., *Biochem.* 28:4929 (1989) and Hampel et al., *Nucl. Acids Res.* 18: 299 (1990), the hepatitis delta virus motif is exemplified in Perrotta and Been, *Biochem.* 31: 16 (1992), an RNAseP motif is described in Guerrier-Takada et al., *Cell* 35:849 (1983), and examples of the group I intron motif are described in Cech et al., U.S. Pat. No. 4,987,071, each of the foregoing disclosures being incorporated herein by reference. These specific motifs are not limiting in the present invention and those of skill in the art will recognize that an enzymatic RNA molecule of the invention has a specific substrate binding site which is complementary to one or more of the target p27 RNA regions and that it has nucleotide sequences within or surrounding that substrate binding site which impart an RNA cleaving activity to the molecule.

The flanking sequences upstream and downstream of the ribozyme catalytic site may comprise segments of any length that effectively imparts the desired degree of targeting specificity for the ribozyme. Preferably a flanking sequence comprises from about 4 to about 24 nucleotides, more preferably from about 6 to about 15 nucleotides, and typically about 9 to 12, and results in base pairing to the substrate sequence immediately upstream and downstream of the p27 RNA sequences which comprise the cleavage site.

The p27 inhibitors may be used alone or in combination may be formulated for a variety of modes of administration. Administration of the inhibitors may include systemic, topical or local administration. Techniques and formulations are generally described in *Remington's Pharmaceutical Sciences*, Mack Publishing Co., Easton, Pa., latest edition. The inhibitor is generally combined with a pharmaceutically acceptable carrier such as a diluent or excipient. Suitable carriers may include fillers, extenders, binders, wetting agents, disintegrants, surface-active agents or lubricants. The choice of such ingredients will depend on the mode of administration and dosage forms. Typical dosage forms include tablets, powders, liquid preparation including suspensions, emulsions, and solutions, granules, capsules and suppositories. Liquid preparation for injection are also typical and include liposome preparations.

A sequence comprising or encoding an oligonucleotide p27 inhibitor, e.g., triplex forming oligonucleotides, antisense oligonucleotide, ribozyme, etc., or a combination of such inhibitors targeted to different portions of the p27 DNA or corresponding RNA can be delivered in a wide variety of ways to targeted cells to facilitate progression of the cell cycle. The oligonucleotides can be administered as synthetic oligonucleotides or expressed from an expression vector. The oligonucleotide can be administered ex vivo, i.e., contacted with target cells that have been removed from an individual or other cell source, treated and returned, or the oligonucleotide molecule can be administered in vivo. When administered ex vivo typically the target cells are exposed to mitogens, e.g., serum mitogens (SCF, IL-3, EPO, TPO, etc.) or the like depending on particular cell population.

Delivery to the targeted cell population can be via an appropriate delivery vehicle, e.g., a liposome, a controlled release vehicle, by use of iontophoresis, electroporation or ion paired molecules, or covalently attached adducts, and other pharmacologically acceptable methods of delivery. Preferably a carrier provides a means to accumulate the oligonucleotide within or at a desired cell population. The delivery vehicle can be designed to serve as a slow release reservoir or to deliver its contents directly to the target cell. Examples of oligonucleotide delivery vehicles include liposomes, hydrogels, cyclodextrins, biodegradable nanocapsules, and microspheres. Liposomes can readily be targeted to the various tissues or cell populations. In another embodiment the anti-p27 oligonucleotide is administered via an expression vector that is suitable for delivery and expression of an oligonucleotide comprising said oligonucleotide in a mammalian host cell.

For in vivo use, routes of oligonucleotide administration include intramuscular, aerosol, intravenous, parenteral, intraperitoneal, etc. The specific delivery route for a selected oligonucleotide will depend on a variety of factors, such as the form of the oligonucleotide, the intended target, the condition being treated, etc. For example, while unmodified oligonucleotide is taken up by cells, modifications can be made to enhance cellular uptake, e.g., by reducing the oligonucleotide's charge to produce a molecule which is able to diffuse across the cell membrane. The structural requirements necessary to maintain oligonucleotide activity are generally recognized in the art. Modifications to enhance cellular delivery can also be designed to reduce susceptibility to nuclease degradation.

The dosage of oligonucleotide inhibitor will also depend on a variety of factors, such as the form of the oligonucleotide, the route of administration, the stage of the cell cycle, the percentage of non-dividing cells in a selected population, whether terminal differentiation has been reached, etc., and thus can vary widely. Generally the dosage will result in complete inhibition of p27 activity or levels sufficiently low within the targeted cells sufficient to permit activation of the cyclin E- and/or cyclin A-Cdk2 complexes and progression of the cell cycle. Establishment of effective levels of p27 inhibitor within a targeted cell population depends upon, e.g., the rate of uptake (or expression by a particular vector), and rate at which the inhibitor is degraded. The duration of treatment may extend for a time sufficient to permit, e.g., transduction of a relatively high percentage of dividing cells compared to an untreated control cell population, but usually will be at least for about 2-4 days, sometimes 6-10 days, although longer durations may be necessary for quiescent or terminally differentiated cell populations. The number and timing of doses can vary considerably, depending on the factors discussed above and the efficacy of a particular inhibitor or mixture thereof, the delivery vehicle and route of administration, etc.

For nucleotide inhibitors of p27 such as p27 antisense oligonucleotides or p27-specific triplex forming oligonucleotides, it may be preferable in include an effective concentration of a lipid formulation with the oligonucleotide of the present invention. Suitable lipid formulations and concentrations are those that enhance the uptake of the oligonucleotides by cells. Such lipids include cationic lipids used for lipofection such as N-[1-(2,3-dioleyloxy)propyl-N,N,N-trimethylammonium chloride (DOTMA) and dioleoyl phophatidylethanolamine (DOPE). One skilled in the art may determine the particular lipid formulation or concentration that will be effective for enhancing the uptake of the oligonucleotide.

Within the methods described in detail herein, the p27 inhibitors may be used in combination with other compounds that inhibit cells from entering cell cycle arrest or which inhibit differentiation that may accompany the proliferation of certain cells. Retinoic acid receptor antagonists, for example, may be used in combination with the disclosed methods and compositions to increase the number of proliferating cells in a cell population. The retinoic acid receptor α antagonist Ro 41-5253 (Apfel et al., *Proc. Natl. Acad. Sci. USA* 89: 7129-7133, 1992) has been shown to counteract the retinoic acid-induced differentiation of the promyelocytic cell line HL-60. Alternatively, antagonists of mitotic inhibitors such as p14 (Guan et al., *Genes Dev.* 8: 2939-2952 (1994)), p15 (Hannon and Beach, *Nature* 371: 257-261 (1994)), p16 (Okamoto et al., *Cancer Research* 55: 1448-151 (1995) and Serrano et al., *Nature* 366: 704-707 (1993)), p18 (Guan et al., ibid.), p19 (Chan et al., *Mol. Cell. Biol.* 15: 2682-2688 (1995) and Zhang et al., *Cell* 82: 915-925 (1995)) and p21 (Harper et al., *Cell* 805-816 (1993) may be used in combination with the p27 inhibitors of the present invention to increase the proportion of proliferating cells in a cell population. Antagonists of these mitotic inhibitors include, but are not limited to, agents that interfere with the transcription or translation of the inhibitors, destruction of the protein, and direct inhibitors of the protein. As such, inhibitors of mitotic inhibitors may include chemical compound inhibitors of the mitotic inhibitors, protein or peptide mitotic inhibitor antagonists, triplex forming oligonucleotides and antisense molecules that inhibit the expression of the mitotic inhibitors, ribozymes, etc.

The methods of the present invention are particularly useful for gene therapy. Target cells for gene therapy are exposed to p27 inhibitors under suitable conditions and for a time sufficient to increase the proportion of dividing cells in the target cell population. The dividing cells are then exposed to a suitable viral vector comprising a gene of interest. Within one embodiment, the cells are exposed to the p27 inhibitor and the viral vector concurrently. Suitable viral vectors include retroviral vectors (see Miller, *Curr. Top. Microbiol. Immunol.* 158: 1-24 (1992); Salmons and Gunzburg, *Human Gene Therapy* 4: 129-141 (1993); Miller et al., *Methods in Enzymology* 217: 581-599, (1994)) and adeno-associated vectors (reviewed in Carter, *Curr. Opinion Biotech.* 3: 533-539 (1992); Muzcyzka, *Curr. Top. Microbiol. Immunol.* 158: 97-129 (1992)). Other viral vectors that may be used within the methods include adenoviral vectors, herpes viral vectors and Sindbis viral vectors, as generally described in, e.g., Jolly, *Cancer Gene Therapy* 1:51-64 (1994); Latchman, *Molec. Biotechnol.* 2:179-195 (1994); and Johanning et al., *Nucl. Acids Res.* 23:1495-1501 (1995), each incorporated herein by reference). The choice of vector will rely in part on the cell type targeted, the disease state that is being treated and the size of the gene to be transferred.

Cells which are exposed to a p27 inhibitor in an amount and for a time sufficient to inhibit exit from the cell cycle can be treated by a variety of substances that target dividing cells. In one embodiment, for example, a cell population in which the proportion of dividing cells has been increased by a p27 inhibitor are more efficiently transduced or transfected with a nucleotide sequence encoding a gene product of interest. Thus, the methods described herein increase the efficiency of gene therapy techniques. For example, target cells treated with a p27 inhibitor are transduced with at least one gene encoding an expression product of interest, typically an RNA or protein molecule. The encoded RNA or protein is one which confers a benefit to the cell population or host being treated, either directly or indirectly. The gene may encode a secreted or non-secreted protein, or an active portion thereof. The selection of a suitable gene for the condition being treated will depend on the condition being treated or prevented and other factors apparent to those skilled in the art. By "gene" is meant DNA that encodes a desired product, such as, for example, a cytokine, a clotting factor, a hormone, an enzyme, a transport protein, a regulatory protein, a structural protein, a receptor, an antigen, ribozyme, antisense molecule, etc. Representative examples of genes for introducing into humans are those encoding human erythropoietin (described in U.S. Pat. No. 4,703,008), human G-CSF, human GM-CSF (Anderson et al., *Proc. Natl. Acad. Sci. USA* 82:6250 (1985)), plasminogen activator, urokinase, insulin (e.g., human insulin as described in U.S. Pat. No. 4,652,525 or proinsulin described in U.S. Pat. No. 4,431,740), interleukins (e.g., interleukin-1, interleukin-2 [described in U.S. Pat. No. 4,738, 927], interleukin-3 [described in EP Publ. 275,598 and 282, 185], interleukin-4, interleukin-7 [U.S. Pat. No. 4,965,195], etc.), interferons, Factor VIII, Factor IX, von Willebrand Factor, ADA, human growth hormone (described in U.S. Pat. No. 4,342,832), etc., analogs and fusions thereof (e.g., fusions of GM-CSF and IL-3 [U.S. Pat. No. 5,108,910]. Each of the foregoing patents and publications is expressly incorporated herein by reference.

It is possible and may be desirable in some instances to employ a mixture of cells treated with a p27 inhibitor, which include a first group transduced with a gene of interest and a second group transduced with a second, different gene of interest. Alternatively, the treated cells may be transduced with more than one gene of interest.

The genes are transduced or transfected into the target cell population which has been treated with a p27 inhibitor using well established protocols. Typically the gene transfer vector will be a retroviral vector, but other vectors may also be employed, e.g., adenovirus vectors (e.g., Rosenfeld et al., *Cell* 68: 143-155 (1992) and Curiel et al., *Proc. Natl. Acad. Sci. USA* 88: 8850-8854 (1991), adenovirus associated vectors (e.g., Muzyczka, *Curr. Top. Microbiol. Immunol.* 158: 97-129 (1992), and as reviewed by Miller, *Nature* 357: 455-460 (1992), which publications are incorporated herein by reference). The construction of retroviral vectors has been described, e.g., Miller and Rosman, *Biotechniques* 7: 980-990 (1989); Adam et al., *J. Virol.* 65: 4985-4990 (1991); Miller, *Curr. Top. Microbiol. Immunol.* 158: 1-24 (1992); and UK Patent publication GB 2,269,175A, each of which is incorporated herein by reference. A preferred retroviral vector is made using PA317 amphotropic retrovirus packaging cells, as described in Miller, U.S. Pat. No. 4,861,719, incorporated herein by reference.

When the cell population treated with p27 inhibitor is transduced or transfected ex vivo with a gene of interest, cells containing the desired gene(s) are often cultured, typically in the presence of a selection agent, e.g., G418, neomycin or the like depending on the selectable marker used in the vector, and then may be returned to the host or expanded until a sufficient number of cells are available for return to the host.

The compositions and methods of the present invention are used to treat a wide variety of cell types. Among those most often targeted for gene therapy are hematopoietic precursor (stem) cells. Other cells include those of which a proportion of the targeted cells are nondividing or slow dividing. These include, for example fibroblasts, keratinocytes, endothelial cells, skeletal and smooth muscle cells, osteoblasts, neurons, quiescent lymphocytes, terminally differentiated cells, slow or non-cycling primary cells, etc. The methods and compositions can be employed with cells of a wide variety of vertebrates, including mammals, and especially those of veterinary importance, e.g. canine, feline, equine, bovine, ovine, caprine, rodent, lagomorph, swine, etc., in addition to human cell populations.

The present invention is particularly preferred for increasing the proportion of dividing cells in a population of hematopoietic precursor cells, especially those of human and other mammals, either ex vivo or in vivo. In an ex vivo method, hematopoietic precursor cells are separated from a blood product, such as bone marrow, peripheral blood, or umbilical cord blood of a donor, fetal peripheral blood and other sources. Such separation may be performed, for example, by immunoselection on the basis of their expression of an antigen, such as the CD34 antigen which is present on substantially all human hematopoietic precursor cells, but is substantially absent from more mature hematopoietic cells. The separated hematopoietic precursor cells may be stored frozen and thawed at a later date for inoculation into a suitable vessel containing a culture medium comprising a nutritive medium. Alternatively, the separated cells may be inoculated directly into culture without first freezing. In both cases the resultant cell suspension is cultured with a p27 inhibitor as described herein under conditions and for a time sufficient to increase the proportion of dividing hematopoietic precursor cells relative to the proportion of such cells present initially in the blood product. The cells may then be treated with vector capable of expressing the gene product of interest. The cells may then be infused or implanted into a host or stored frozen for infusion at a later date.

In addition, the methods of the present invention may be used in vitro to create novel stem cell lines. According to this aspect of the invention the p27 inhibitor is administered to a cell population, thereby preventing cells from exiting the cell cycle and increasing the percentage of cells in the cell cycle, and may also reduce the need to include exogenous serum mitogens. The methods may also be used in combination with, for example, methods for creating stem cell lines by exposing the cell population to a p27 antagonist under suitable conditions and for a time sufficient to increase the population of dividing cells, and exposing the dividing cells to a suitable expression vector comprising an gene encoding a desired gene product such that the resulting cells express the gene product and are self-renewing.

The following examples are offered by way of illustration, not by way of limitation.

EXAMPLE I

Subconfluent, exponentially asynchronous proliferating Balb/c-3T3 fibroblasts (Rb wild type; p53 status unknown) in media containing 10% fetal calf serum were rinsed once with serum-free medium and transferred to low serum medium containing mitogens (0.1% serum). Flow cytometry analysis (Firpo et al., *Mol. Cell. Biol.* 14:4889 (1994)) demonstrated that within 24 hours, approximately the length of one cell cycle, 95% of the cells arrested in G1, indicating that these cells require a mitogenic signal to proceed through each division cycle. G1 arrest correlated with a 6 to 8 fold induction of the p27$^{Kip1}$ protein as determined by immunoblot analysis (Nourse et al., *Nature* 372:570 (1994); Kato et al., *Cell* 79:487 (1994)) of proliferating and serum-starved cells. Similar increases in p27 expression occur in primary human diploid fibroblasts deprived of serum mitogens, and in primary human T lymphocytes following withdrawal of IL-2, indicating that this is a common pattern of p27 expression in normal, non-transformed cells (Nourse, ibid., Kato, ibid.).

It was then shown that in Balb/c-3T3 cells p27 levels start to increase within 4 hours of serum withdrawal, reach 60% of maximal levels within 12 hours, and peak by 24 hours. Proliferating Balb/c-3T3 fibroblasts were rinsed in serum-free medium and re-fed with low serum medium containing 0.1% serum. p27 western blots (ECL, Amersham) were performed on cells harvested at 4, 8, 12, 16 and 24 hours after re-feeding. p27 levels started to increase at 4 hours and were 60% of maximal at 12 hours). Thus, the induction of p27 protein parallels the accumulation of the initially asynchronous cell population in G1, and indicates a critical role in the early events associated with exit from the cell cycle.

Histone H1 kinase assays were performed on cyclin A, cyclin E and Cdk2 (Firpo et al., *Mol. Cell. Biol.* 14: 4889 (1994)) immunoprecipitated from extracts made from proliferating and serum-starved Balb/c-3T3 cells. The results showed that cell cycle arrest of Balb/c-3T3 cells was correlated with downregulation of the cyclin E-Cdk2 and cyclin A-Cdk2 protein kinases, and this appeared to be related to induction of p27. Both cyclin E-Cdk2 and cyclin A-Cdk2 were associated with increased amounts of p27 following mitogen withdrawal. Immunodepletion experiments were also performed to determine the amount of cyclin E bound to p27. Cell extracts from asynchronously proliferating Balb/c-3T3 cells and Balb/c-3T3 cells that had been serum-starved for 24 hours were depleted for p27 by incubating 100 ug of each extract with p27 antiserum and protein A agarose for 1 hour at 4° C., centrifuging the immunoprecipitates for 5 seconds at 13,000 r.p.m and immunodepleting the remaining unbound supernatant twice more with p27 antiserum and protein A agarose. The immunodepleted extracts (α p27) were analyzed by cyclin E (Ohtsubo and Roberts, *Science* 259: 1908 (1993); Matsushime et al., *Cell* 65: 701 (1991); Koff et al., *Science* 257:1689 (1992)) and p27 immunoblots and compared to undepleted extracts and extracts depleted with p27 preimmune sera. The results showed that only a small portion of cyclin E in proliferating cells was bound to p27, while all the cyclin E in arrested cells was bound to p27. Similar results were obtained for cyclin A: Experiments were performed as for cyclin E, except that cyclin A and p27 immunoblots were performed on extracts depleted for p27. All of the cyclin A was bound to p27 in extracts from serum-starved cells while only a small fraction (5%) of cyclin A was associated with p27 in proliferating cells).

In sum, Balb/c-3T3 fibroblasts arrest in the first G1 following mitogen withdrawal, and this correlates with increased expression of p27, increased association of p27 with cyclins E and A, and inactivation of the cyclin E- and cyclin A-Cdk2 kinases.

The relationship between p27 expression and cell proliferation was studied by testing the relative abilities of specific serum mitogens to both downregulate p27 and induce cell proliferation. Flow cytometry analysis was performed on both the asynchronously proliferating Balb/c-3T3 cells (Hi serum) and subconfluent Balb/c-3T3 cells that had been serum-starved for 24 hours (Low serum) in the presence of either individual growth factors (PDGF, IGF-1 or EGF) or all three growth factors (PIE) (see Table). p27 immunoblots were performed on cell extracts (10 ug) from cells treated with growth factors. Only PDGF was able to prevent G1 arrest, and only PDGF prevented the induction of p27. Balb/c-3T3 fibroblasts grown at high density have more complex mitogen requirements than when grown subconfluently; no single mitogen is able to cause proliferation of cells at high density. Instead, PDGF initially stimulates the density arrested, quiescent cells to become "competent" to respond to "progression" factors, IGF-1 and EGF (Pledger et al., *Proc. Natl. Acad. Sci. USA* 74:4481 (1977); Leof et al., *Exp. Cell Res.* 147:202 (1983)). Therefore, under these conditions passage through the restriction point does not occur until cells have been exposed to all three mitogens.

It was also observed that in density-arrested cells PDGF alone was insufficient to alter p27 abundance; rather p27 levels declined once cells became committed to proliferate in response to the complete mitogenic signal provided by the combined action of PDGF, EGF and IGF-1. Density-arrested Balb/c-3T3 fibroblasts were rinsed in serum-free medium and were re-fed with low serum medium containing 0.1% serum and 10 ng/ml of either PDGF, IGF, EGF, IGF and EGF, or all three growth factors. Cells were harvested 24 hours later and were analyzed by flow cytometry for DNA content and also by p27 immunoblot. The results indicated that a combination of all three growth factors was required to stimulate 70% of the cells to enter the cell cycle and to decrease p27 levels by ten-fold.

Thus, under two different growth arrest conditions the ability of specific mitogens to stimulate passage through the restriction point correlated with their ability to regulate p27. These results showed that p27 is not necessarily a downstream effector for any particular mitogen. Rather, decreased expression of p27 reflects the integrated action of the collection of mitogens required for cell proliferation.

EXAMPLE II

The observed correlation between p27 regulation and mitogenic signaling was extended by using anti-sense oligonucleotides to block expression of the p27 protein. This showed that regulation of p27 was necessary for cell cycle control by serum mitogens.

Phosphorothioate oligonucleotides were modified by the addition of a propyl group to the pyrimidine bases, which is thought to enhance base stacking and facilitate the sense-antisense interaction (Raviprakash et al., *J. Virol.* 69:69 (1995)). The oligonucleotides were synthesized by the H-phosphonate method on an automated synthesizer (model 8750, Milligen Bioresearch, Bedford, Mass.) using standard chemistry on controlled pore glass (CPG) support. The nucleoside analogs were prepared as previously described (B. Froehler, Protocols for oligonucleotides and Analogs: Synthesis and Properties. Humana, Totowa, N.J. (1993); Froehler et al., *Tetrahedron Lett.* 33:5307 (1992); and Froehler et al., *Tetrahedron Lett.* 34: 1003 (1993)). The antisense oligonucleotides were designed to target sequences that are identical between the mouse and the human p27 sequences, which are described in WO PCT/US95/07361 and deposited with Genbank under accession nos. U09968 and U10906, respectively.

The antisense oligonucleotide sequences used in these experiments oligonucleotide 3163 ([SEQ ID NO:1] 5' UGG CUC UCC UGC GCC 3') (targets base pair 306-320 of murine Kip1, the sequence of which is described in WO PCT/US95/07361, incorporated herein by reference, and is also deposited with Genbank under Accession Number U09968) and its mismatch control oligonucleotide 3436 ([SEQ ID NO:2] 5' UCC CUU UGG CGC GCC 3'), and oligonucleotide 3162 ([SEQ ID NO:3] 5' GCG UCU GCU CCA CAG 3') (targets base pair 548-562 of murine Kip1, the sequence of which is described in WO PCT/US95/07361, incorporated herein by reference and deposited with Genbank under Accession Number U09968) and its mismatch control oligonucleotide 3437 ([SEQ ID NO:4] 5' GCA UCC CCU GUG CAG 3'). The mismatch control oligonucleotides were designed to have the same base composition as the antisense oligonucleotides but with scrambled nucleotide sequences.

Oligonucleotides were efficiently delivered to cells by association with a lipophilic reagent, dioleoyl phosphotidylethanolamine (DOPE). For the lipofection procedure 30 nM of each oligonucleotide was mixed with 2.5 ug/ml of DOPE (2:1) (Gilead Sciences, Inc., Foster City, Calif.) in serum-free medium and incubated for 10 minutes at 37° C. Proliferating Balb/c-3T3 fibroblasts were rinsed once in serum-free medium and re-fed with the oligonucleotide/DOPE solution in low serum medium containing 0.1% serum. The cells were then incubated for 24 hours in humidified incubators at 37° C. with 5% $CO_2$.

The percentage of cells that took up the oligonucleotides was determined by lipofecting proliferating Balb/c-3T3 cells with an FITC-tagged random oligonucleotide (Gilead Sciences, Inc.) for 6 hours with subsequent re-feeding with low serum medium containing 0.1% serum for 24 hours. The percentage of cells that were positive for uptake of the FITC-tagged oligonucleotides was determined by UV fluorescent microscopy. The use of the FITC-labeled oligonucleotide control showed that 90-95% of the cells took up and concentrated the oligonucleotides in the cell nucleus.

Cell extracts from the serum-starved (24 hours in low serum medium containing 0.1% serum) Balb/c-3T3 fibroblasts transfected with the p27 antisense or mismatch control oligonucleotides were analyzed by immunoblotting with anti-p27 antiserum. The immunoblots showed that expression of p27 protein was substantially decreased in the antisense treated cells (FIG. 1A) while the mismatch oligonucleotide had no effect on accumulation of p27 following serum withdrawal. While the results were shown for one antisense and one control oligonucleotide, identical results were obtained with the other antisense and control oligonucleotides.

p27 antisense treatment did not decrease expression of the related CKI, p21. Proliferating Balb/c-3T3 fibroblasts were lipofected with antisense and mismatch oligonucleotides as described above. Cells were re-fed with low serum medium containing 0.1% serum and were analyzed 24 hours later by flow cytometry and p21 immunoblots. As observed in Firpo et al., *Mol. Cell. Biol.* 14:4889 (1994), p21 levels were elevated in proliferating cells as compared to serum-starved cells. Cells lipofected with either p27 mismatch or antisense oligonucleotides expressed slightly higher levels of p21 as compared to serum-starved control cells.

Figure 1B:
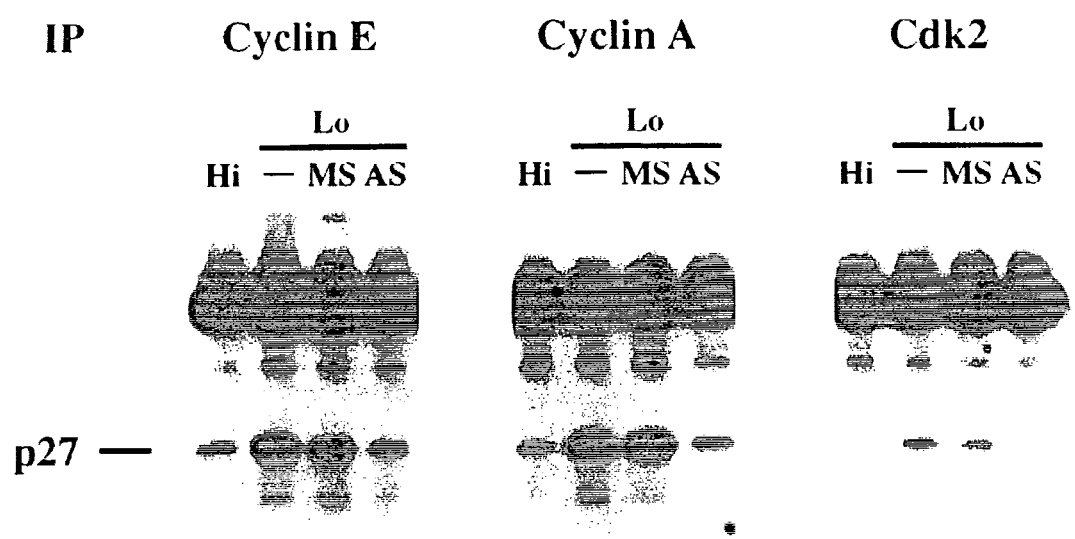
FIG. 1B is a p27 immunoblot analysis of cyclin A, cyclin E or Cdk2 immunoprecipitates from proliferating Balb/c-3T3 cells (HI), subconfluent serum starved Balb/c-3T3 cells (Lo) or Balb/c-3T3 cells serum starved for 24 h following lipofection with either mismatch (MS) or p27 antisense oligonucleotides (AS).

A decrease in the association of p27 with cyclin A and cyclin E corresponded to the decrease in overall levels of p27 in the antisense-treated cells (FIG. 1B). This was associated with restoration of cyclin E and cyclin A-associated kinase activities in serum-starved cells. Proliferating Balb/c-3T3 fibroblasts were lipofected with either p27 mismatch or antisense oligonucleotides for 6 hours and were then re-fed with low serum medium containing 0.1% serum. 24 hours later the cells were harvested, and Histone H1 kinase assays were performed on cyclin E and cyclin A immunoprecipitates. Serum-starved cells lipofected with p27 antisense oligonucleotides contained elevated levels of cyclin E and cyclin A associated Histone H1 kinase activity as compared to serum-starved cells.

In a proliferating population of Balb/c-3T3 fibroblasts 27% of the cells are in S phase, and this falls to about 9% of cells within 24 hours following serum withdrawal (Table). Flow cytometry of subconfluent Balb/c-3T3 cells serum-starved for 24 hours after lipofection with either p27 mismatch or antisense oligonucleotides as described above showed that cells exposed to the mismatch oligonucleotide behaved identically to control cells. However, cells exposed to p27 antisense oligonucleotides did not undergo G1 arrest after serum withdrawal; 23% of the cells remained in S phase (Table). p27 antisense oligonucleotides also prevented the osteosarcoma cell line SAOS-2 (Rb mutated; p53 mutated) from exiting the cell cycle in response to serum withdrawal (Table). This demonstrated that the requirement for p27 is manifest in more than one cell type, and that p27 is required for mitogen responsiveness independently of the Rb status of the cell.

TABLE

Data for experiments using flow cytometry. Flow cytometry analysis was performed as described in Firpo et al., Mol. Cell. Biol. 14:4889 (1994). The data are presented as the percentage of cells in each phase of the cell cycle.

| Cell Type/Condition | G1 | S | G2/M |
|---|---|---|---|
| Balb/c-3T3 | | | |
| Hi Serum | 63.7 | 27.4 | 8.9 |
| Low serum | 86.9 | 9.3* | 3.9 |
| MSM/Lo | 81.7 | 11.6 | 6.7 |
| AS/Lo | 62.2 | 23.4 | 14.4 |
| MSM/Hi | 59.2 | 26.8 | 14.1 |
| AS/Hi | 42.3 | 35.1 | 22.6 |
| PDGF | 69.4 | 21.4 | 9.2 |
| IGF | 83.2 | 7.7 | 9.1 |
| EGF | 90.5 | 3.4 | 6.1 |
| PDGF/IGF/EGF | 64.2 | 23.8 | 11.9 |
| SAOS-2 | | | |
| Hi Serum | 54.3 | 25.8 | 19.9 |
| Low Serum | 70.6 | 13.6 | 15.8 |
| MSM/Lo | 60.5 | 16.8 | 22.7 |
| AS/Lo | 44.2 | 27.9 | 27.9 |

*Flow cytometry analysis overestimated the percentage of cells in S phase. BrdU staining demonstrated that under low serum conditions 25% of the cells were in S phase.

Incorporation of bromodeoxyuridine (BrdU, Amersham) and tritiated thymidine into nuclear DNA were used as independent measures of the effect of p27 antisense on cell cycle progression. Twenty-four hours after serum starvation Balb/c-3T3 cells that had been transfected with either the p27 antisense or mismatch oligonucleotides were pulse-labeled with BrdU for three hours to measure the fraction of cells continuing to transit S phase. The percentage of nuclei stained by uptake by BrdU was determined by immunostaining with anti-BrdU monoclonal antibodies as described by (Ohtsubo and Roberts, ibid.; Matsushime et al., ibid.; and Koff et al., ibid.; which are each incorporated by reference herein). The percent of cells staining positive for BrdU incorporation (percent labeled nuclei) was determined as a percentage of the total number of cells present on a 1 mm coverslip. The transfected cells were labeled with tritiated thymidine essentially as described above with the serum-starved cells being subjected to a three-hour pulse labeling with 1 uCi/mo of tritiated thymidine. The percent of tritiated thymidine incorporation was determined as the percentage of tritiated thymidine incorporated (c.p.m.) into serum-starved and lipofected cells as compared to asynchronously proliferating cells pulse-labeled for three hours with tritiated thymidine. This confirmed that cells exposed to p27 antisense oligonucleotides continued to synthesize DNA for at least 24 hours following serum withdrawal. Of the serum starved cells treated with p27 antisense oligonucleotides, 35% incorporated BrdU into nuclear DNA, while only 2-3% of the cells treated with mismatch control oligonucleotides did so. Analogous results were obtained by using tritiated thymidine incorporation to measure DNA synthesis rates.

In sum, these results show that cells treated with p27 antisense oligonucleotides failed to induce p27 protein in response to mitogen depletion, and were unable to exit the cell cycle. Although the duration of the effect for this antisense preparation was limited, cells treated with p27 antisense expressed low levels of p27 protein and continued to proliferate for at least 48 hours without serum mitogens.

EXAMPLE III

The specificity of antisense oligonucleotides was demonstrated by showing that the effect of the antisense treatment could be overcome by restoring expression of the targeted protein.

The degeneracy of the genetic code was used to construct a p27 expression plasmid which could not be inhibited by the antisense oligonucleotides, but nevertheless encoded wild-type p27 protein (the p27 "wobble" plasmid):

```
                                                     [SEQ ID NO:5]
         (102)   L    A    Q    E    S    (106)

[SEQ ID NO:6]
    p27 Wild type  CTG  GCG  CAG  GAG  AGC

[SEQ ID NO:7]
p27 Wobble Mutant  --T  --A  --A  --A  TCA
```

To construct the p27 "wobble" expression plasmid, a "megaprimer" was generated by PCR amplification using a primer to plasmid sequences (T7 primer) and a primer ([SEQ ID NO:8] 5'TAA AGG CAC CGC CTG GCG ACT ACC GCT GAC GTC CTG TGA TTC TTG TGC AAG CAC CTT GCA GGC GCT C-3') which contains mutations at the wobble positions for the amino acid sequence LAQESQD [SEQ ID NO:9] (amino acids 102-108) of murine p27. The "megaprimer" was subsequently used with a primer to plasmid sequences (T3 primer) at the 3' end to PCR amplify a full length clone which was subcloned into the expression vector pCS2+. These mutations created a p27 sequence with 7 unmatched bases to the p27 antisense oligonucleotide and created a unique Aat II site.

Figure 2A:
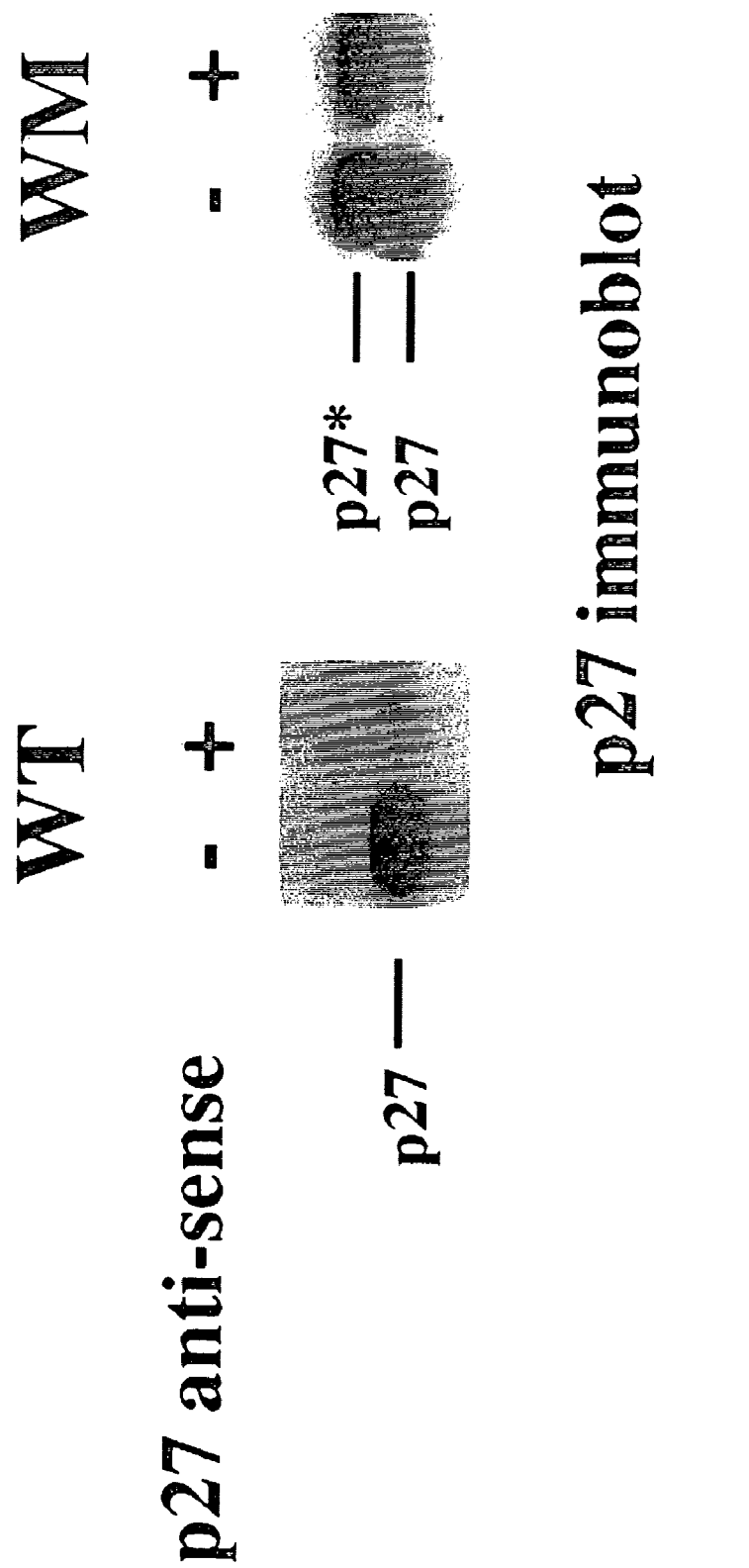
FIG. 2A is a p27 immunoblot analysis of proliferating Balb/c-3T3 cells 24 h after lipofection in the presence (+) or absence (−) of p27 antisense oligonucleotides with plasmid encoding either wild type p27 or tagged (p27*) p27 wobble mutant.

A "tagged" version of the p27 wobble plasmid was also constructed, which encoded an electrophoretic variant of p27 resulting from a single amino acid change outside of the domain targeted by the antisense oligonucleotide. In addition to the base changes listed above for amino acids 102-108, the p27 "tagged" wobble mutant also contained mutations at Serine (111) and Arginine (112). These amino acids were converted to Threonine and Serine, respectively resulting in a p27 wobble mutant that migrates slightly slower than endogenous murine p27 and exogenous wild type p27. The tagged p27 could be separated and thereby distinguished from endogenous p27, enabling a simultaneous test of the effects of p27 antisense oligonucleotides on expression from the wild type and wobble p27 genes in the same cell.

p27 immunoblot assay were carried out on extracts from proliferating Balb/c-3T3 cells twenty-four hours after lipofection in the presence or absence of p27 antisense oligonucleotides with plasmid encoding either wild type p27 or tagged p27 wobble mutant. It was observed that the p27 antisense oligonucleotides effectively inhibited expression from both an exogenous wild-type p27 gene, and from the endogenous p27 gene, but were unable to inhibit p27 protein expression from the p27 wobble plasmid (FIG. 2A).

Figure 2B:
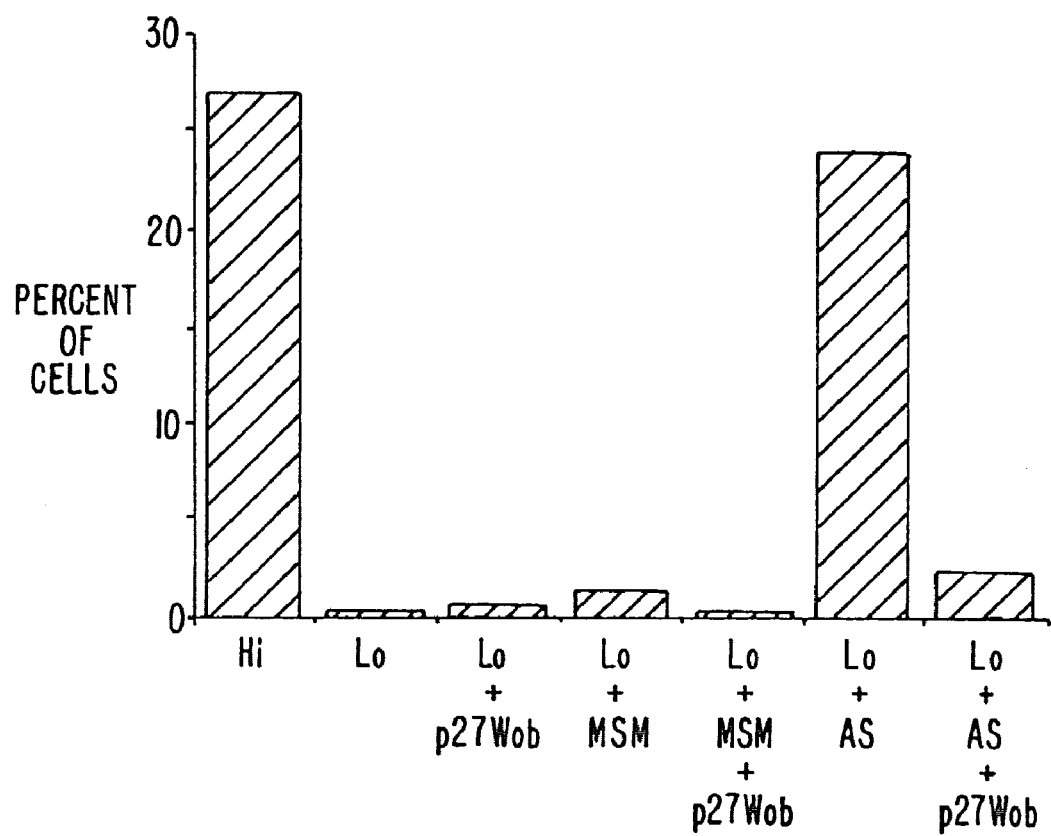
FIG. 2B shows results obtained when proliferating Balb/c-3T3 fibroblasts (Hi) were lipofected with p27 mismatch (MSM) or antisense (AS) oligonucleotides for 6 h in high serum.

A p27 wobble plasmid was then used to determine whether expression of p27 protein in the antisense treated cells renewed their responsiveness to mitogen depletion. These experiments were designed to study the physiological effects of p27 expression, and therefore used a wobble plasmid encoding fully wild type p27, rather than the electrophoretic variant described above. Balb/c-3T3 cells were lipofected with mismatch or p27 antisense oligonucleotides, and then microinjected with a both plasmid encoding β-galactosidase (to mark the injected cells) and with the p27 wobble plasmid. Microinjection, immunofluorescence staining, and fluorescence microscopy were carried out as described in Fisher et al., *Nuc. Acid Res.* 21: 3857 (1993); Hanvey et al., *Science* 258: 1481 (1992); Wagner et al., *Science* 260:1510 (1993); Moulds et al., *Biochem.* 34:5044 (1995), each of which is incorporated herein by reference. Cells were rinsed once in serum-free medium and were then serum-starved in low serum medium containing 0.1% serum for 24 hours. As described above, the cells were pulse-labeled with BrdU for three hours followed by immunostaining for both BrdU and β-galactosidase. For costaining of β-galactosidase and BrdU, the cells were fixed, and then first incubated with a polyclonal anti-β galactosidase antibody (5'3' Inc. Boulder, Colo.) for 60 minutes, followed by incubation with a fluorescein-conjugated goat anti-rabbit IgG (Jackson Immunoresearch Laboratories, West Grove, Pa.) for 30 minutes. The cells were then incubated with a fluorescein-conjugated rabbit anti-goat IgG antibody for 30 minutes. At the end of this procedure, the slides were fixed again with 3.7% formaldehyde for 10 minutes followed by incubation in acetone for 1 minute. The cells were rehydrated with TBS followed by a 10 minute treatment with 4 N HCl and a final wash with TBS. To visualized the BrdU staining, the cells were incubated for 1 hour with a monoclonal anti-BrdU antibody (Boehringer Mannheim, Germany), followed by a 30 minute incubation with a rhodamine-conjugated donkey anti-mouse antibody (Jackson Immunoresearch Laboratories, West Grove, Pa.)). The percentage of cells in S phase measured by pulse labeling with BrdU which was carried out as described above. The percent of β-galactosidase positive cells that incorporated BrdU was determined and expressed as the percent of cells in S phase as compared to the total number of cells staining positive for β-galactosidase expression. Lipofection of cells with p27 antisense oligonucleotides markedly decreased the percentage of cells that withdrew from the cell cycle following mitogen depletion, and this was reversed by microinjection with the p27 wobble plasmid (FIG. 2B).

These results showed that the inability of p27 antisense treated cells to exit the cell cycle after mitogen depletion is specifically caused by the loss of p27 expression.

EXAMPLE IV

The basal level of p27 expressed in proliferating cells may contribute to an inhibitory threshold imposed on Cdk activation during G1 (Sherr and Roberts, *Genes & Dev.* 9:1149 (1995). In mitotically proliferating cells Cdk activation would thus occur when the number of cyclin-Cdk complexes exceeds the CKI threshold. Therefore, the time of Cdk activation during G1 would depend both upon the rate of cyclin synthesis and the level of CKI expression. (Over-expression of G1 cyclins causes early activation of cyclin-Cdk complexes, and a shorter G1. Ohtsubo and Roberts, *Science* 259: 1908 (1993); Quelle et al., *Genes & Dev.* 7: 1559 (1993); Resnitzky and Reed, *Mol. Cell. Biol.* 15:3463 (1995)).

This Example describes experiments which indicate that a p27 threshold influences the timing of Cdk activation, and therefore the duration of G1. At one extreme, high levels of p27 have been shown to prevent Cdk activation and arrest the cell cycle in G1 (Polyak et al., *Cell* 78: 59 (1994), Toyashima and Hunter, ibid., p. 67).

To determine whether decreased p27 expression allowed premature Cdk activation and a shortened G1, exponentially proliferating Balb/c-3T3 cells were lipofected with p27 antisense or mismatch control oligonucleotides and allowed to continue to proliferate in high serum for an additional 24 hours.

The p27 antisense treatment was observed to decrease p27 protein expression in proliferating cells well below the normal basal level, while no effect was seen on p27 expression in the mismatch control. Analysis of these cell populations by flow cytometry revealed that p27 antisense oligonucleotides markedly decreased the percentage of cells in G1, indicating that the length of G1 has been shortened relative to other phases of the cell cycle. This supports the conclusion that the level of p27 expressed in proliferating cells contributes to the length of G1.

EXAMPLE V

A targeted deletion of the p27 gene was created in transgenic mice and viable homozygous p27 "knock-out" animals wherein the p27 locus is functionally inactivated by a structural disruption of the gene were produced.

The knock-out mice, in which the p27 gene coding sequence was replaced with the neomycin resistance gene, were generated to determine the effect of such a deletion in homozygous and heterozygous mice. The genomic p27 sequences were derived from the 129/Sv strain of mice so that the homologous recombination could take place in a congenic background in 129/Sv mouse embryonic stem cells. A p27 genomic clone was isolated from a genomic library prepared from 129/Sv mice (Soriano et al., *Cell* 64: 693-707 (1991); which is incorporated by reference herein) using a $^{32}$p-radiolabeled p27 cDNA probe. Plasmid pPNT (Tybulewicz et al., *Cell* 65: 1153-1163 (1991), which is incorporated herein by reference in its entirety) containing the neomycin resistance gene (neo, a positive selection marker) and the Herpes simplex virus thymidine kinase gene (hsv-tk; a negative selection marker) under the control of the PGK promoter provided the vector backbone for the targeting construct. A 7 kb Xho I fragment containing the genomic 5' untranslated sequence of p27 was inserted at the Xho I site of the pPNT vector such that the 5' end of the p27 fragment was inserted upstream of the PGK promoter-neo expression cassette. A 1.8 kb Bgl II-Eco RI fragment containing the 3' untranslated p27 genomic sequence was inserted between Bgl II and Eco RI sites, downstream of the PGK promoter-neo expression cassette such that the 5' and 3' of the genomic fragments were in the same orientation. This resulted in a total of 8.8 kb of homology from the flanking regions of p27 with the entire p27 coding region being replaced by the PGK promoter-neo expression cassette from the pPNT vector. In this construct hsv-tk is also driven by the PGK promoter but lies 3' to the p27 flanking DNA and provides a means of selection against random integration events by causing cell death in the presence of 1(2-deoxy-2-fluoro-beta-D-arabinofuranosyl)-5-iodouracil (FIAU, a nucleoside analog).

The targeting construct was linearized and transfected by electroporation into mouse embryonic stem (ES) cells. A 129/Sv derived ES cell line, AK-7, described by Zhuang et al. (*Cell* 79: 875-884 (1994); which is incorporated herein by reference in its entirety) was used for electroporation. These ES cells were routinely cultured on mitomycin C-treated (Sigma) SNL 76/7 STO cells (feeder cells) as described by McMahon and Bradley (*Cell* 62: 1073-1085 (1990); which is incorporated herein by reference in its entirety) in culture medium containing high glucose DMEM supplemented with 15% fetal bovine serum (Hyclone) and 0.1 mM β-mercaptoethanol.

To prepare the targeting construct for transfection, 25 μg of the targeting construct was linearized by digestion with Hind III, phenol-chloroform extracted, and ethanol precipitated. The linearized vector was then electroporated into $10^7$ ES cells. The electroporated cells were seeded onto two gelatinized plates with a subconfluent layer of mitomycin-C inactivated SNL 76/7 STO feeder cells. Twenty-four hours post-electroporation, one plate received medium containing 0.2 mM G418 and the remaining plate received 0.2 mM G418 and 0.2 mM FIAU. The presence of FIAU provided approximately a 10-fold reduction in the number of colonies formed in comparison to control plates with G418 alone. The culture medium for each plate was changed every day for the first few days, and then changed as needed after selection had occurred. Colonies of ES cells with true homologous recombination (HR) events, in which p27 gene was replaced with the neo gene, were identified by the ability to amplify a 2 kb PCR fragment unique to the p27-knock-out construct. After 10 days of selection, a portion of each colony was picked microscopically with a drawn micropipette, and was directly analyzed by PCR as described by Joyner et al. (*Nature* 338: 153-156 (1989); which is incorporated herein by reference in its entirety). Briefly, PCR amplification was performed as described (Kogan et al., *New England J. Med.* 317: 985-990 (1987); which is incorporated herein by reference in its entirety) using 4 cycles of 93° C. for 30 seconds, 36 cycles of 93° C. for 30 seconds, 55° C. for 30 seconds, and 65° C. for 2 minutes. To detect the mutant p27 allele, primers neo-1 (CCT TCT ATG GCC TCC TTG ACG) and mgK2 (TTC TTA CCG AAA GGG ACA CTA ATC) [SEQ ID Nos:10 and 11, respectively] were used in the PCR reaction. Positive colonies, identified by PCR, were subcloned into 4-well plates, expanded into 60 mm plates and frozen into 2-3 ampules. Southern blot analysis using probes external to both the 5' and 3' end of the targeting construct confirmed that a true homologous recombination event had occurred in each of 12 clones surveyed.

To generate chimeric mice, 6 positive clones were trypsinized into single cells, and blastocysts obtained from C57BL/6J mice were each injected with approximately 15 cells from an individual clone. The injected blastocysts were then implanted into pseudopregnant F1 mice (C57BL/6J× 129/Sv). Chimeric pups with predominantly agouti coats (indicating a major contribution of the ES cells to the somatic tissues) were selected for further breeding. Nine complete male chimeras were subsequently identified representing three separate ES cell clones. The male chimeras were bred to C57BL/6J females. The chimeric males were also bred to 129/Sv females to place the knock-out mutation in a congenic background.

The transmission of the mutant p27 transgene in 50% of the F1 agouti progeny was again shown with PCR. Briefly, genomic DNA prepared from tail biopsies was subjected to PCR as described above using primers mgK-3 (TGG AAC CCT GTG CCA TCT CTA T) and neo-1 [SEQ ID Nos:12 and 10] to identify the mutant (p27 knock-out gene) and primers mgk-3 and mck-5 (GAG CAG ACG CCC AAG AAG C) [SEQ ID Nos:12 and 13] to identify the wild-type gene. Homozygous p27 deletions were obtained in the F2 generation as confirmed by the absence of a the ability to PCR a 0.5 kb fragment unique to the mutant transgene and the absence of a 0.9 kb wildtype fragment. The complete absence of p27 protein from these mice was confirmed on Western blots of whole tissue extracts using rabbit polyclonal anti-p27 antisera.

In a comparison of mice of each genotype (the homozygous knock-out, $-/-$; the heterozygous knock-out, $-/+$; and wildtype, $+/+$) on the hybrid genetic background (129/Sv× C57BL/6J), a size difference between the homozygous p27 knock-out mice relative to wildtype mice was demonstrated. The hybrid mice (129/Sv×C57BL/6J) from the F2 generation displayed a considerable size variation because the wildtype 129/Sv mice are considerably larger than their C57BL/6J counterparts. However, the homozygous knock-out mice displayed, on average, about 30% greater weight than sex matched wildtype litter mate controls (See, FIGS. 3B and C). This difference was present at 3 weeks of age and persisted to adulthood ($p<0.05$). This size difference has been confirmed in the inbred (129/Sv) background.

Figure 3A:
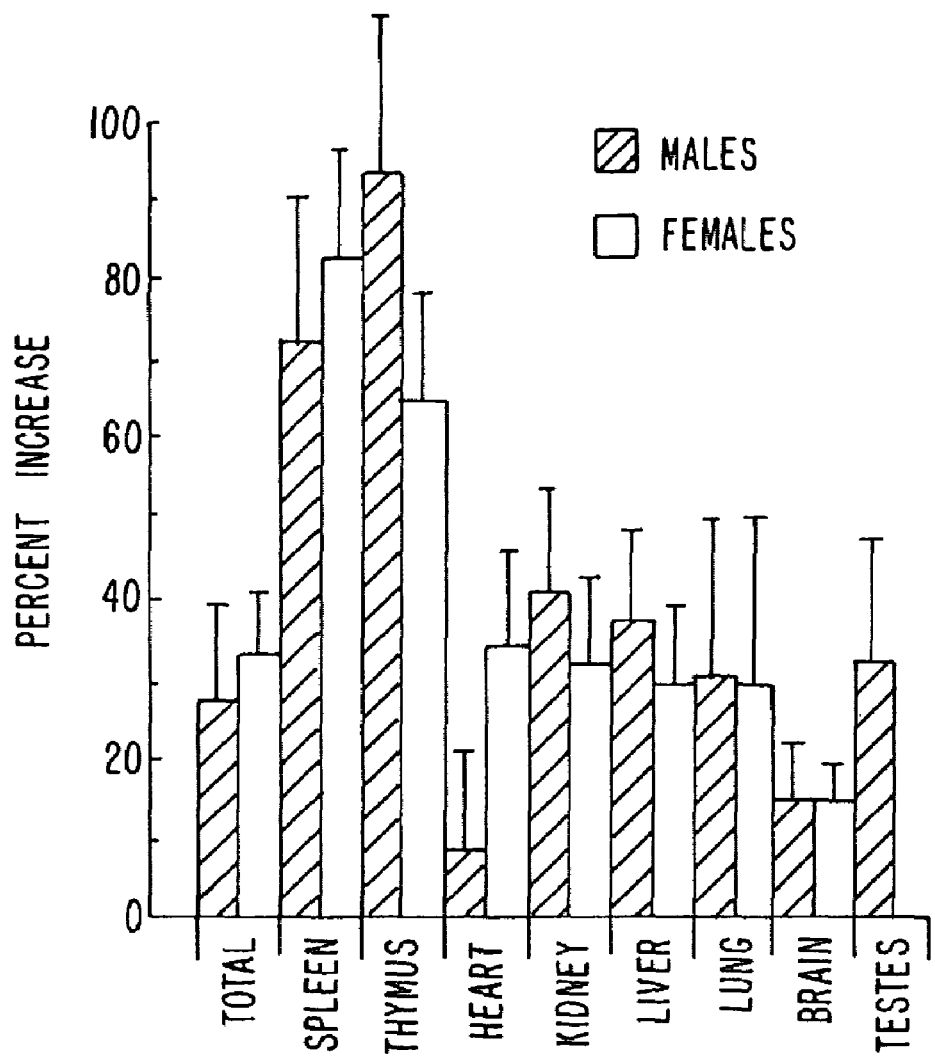
FIG. 3A shows the mean and 95% confidence interval of organ weights from 20 control and p27$^{-/-}$ mice at 6-7 weeks of age, and plotted is percent increase in weight in knockout mice compared with control mice.
Figure 3B:
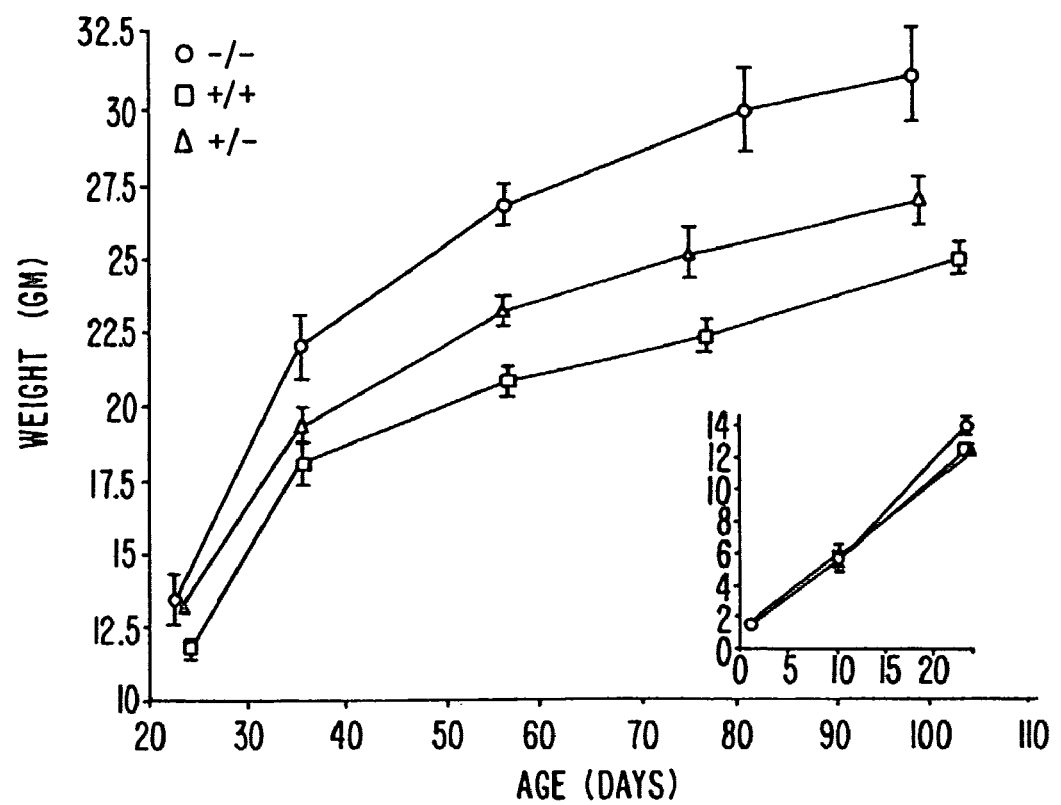
FIG. 3B shows mean and 95% confidence interval of weights of 30 control, p27$^{-/-}$, and p27$^{-/-}$ female mice as a function of age, where the inset shows weights of a separate group of 20 male plus female mice weighed at birth and at 10 days. Data from 21 days is the mean of the results from the first group.
Figure 3C:
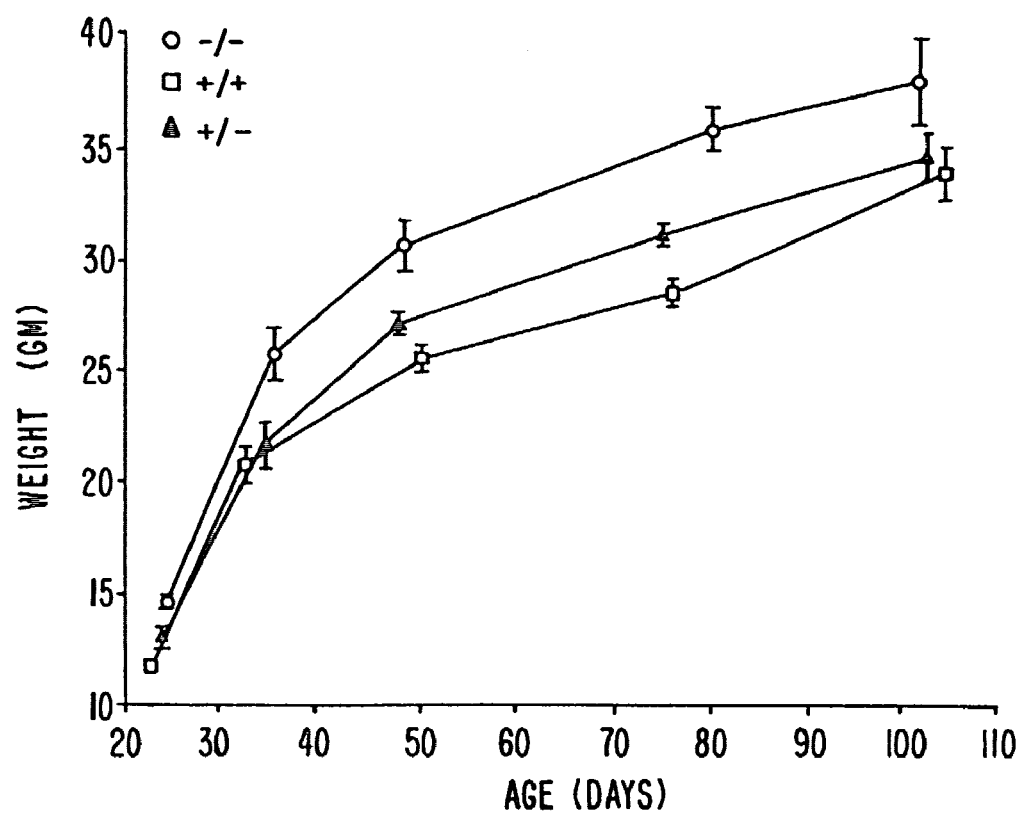
FIG. 3C depicts the same as FIG. C, but data were obtained from male mice.

To further examine the size difference between the knock-out mice and the wildtype mice, internal organs from randomly selected knock-out mice and wildtype litter mate controls were dissected. The weights of internal organs of the knock-out mice were proportional to body size with the notable exception of the thymus and spleen, which on the average were approximately twice as large in the knock-out animals (FIG. 3A). Counts of nucleated cells from the spleen and thymus from the knock-out mice confirmed the hypercellularity of these tissues and were proportional to the weights of the organs. p27 has been shown to be expressed both in the cortex and the more mature medullary areas of the mouse thymus. The increased mass of the thymus and spleen, however, was small in comparison to the overall body weight of the animal and therefore did not account for the weight difference of the animals as a whole. Thus, the p27 deletion appeared to lead to an overall increase in the animals size, without a disproportionate increase in fat or organomegaly.

Splenic CFU-Meg (megakaryocyte colony forming unit), CFU-GM (granulocyte/macrophage colony forming unit), BFU-E (erythroid burst forming unit) were determined on spleens harvested from two wildtype and two homozygous knock-out mice (that were less than a factor of two different in size in weight and total cell number) by colony-forming units assay essentially as described (Kaushansky et al. *Nature* 369: 568-571 (1994); Broudy et al., *Blood* 85: 1719-1726 (1995); Kaushansky et al., *J. Clin. Invest.* 96: 1683-1687 (1995), which are incorporated herein by reference). A comparison of the total number of CFU-Meg, CFU-GM, BFU-E from the spleens of the knock-out and wildtype mice demonstrated up to a 10-fold increase in the number of each of the cell types in the spleens from the knock-out mice relative to the number of each cell type from the spleens of the wildtype mice (Table).

TABLE

| Hematopoetic Colony Formation[a] | | | | |
|---|---|---|---|---|
| | CFU-GM | CFU-E | CFU-MK | BFU-E |
| Femur | | | | |
| Wildtype | 25.5 ± 1.2 | 88.0 ± 14.7 | 4.42 ± 0.73 | 2.60 ± 0.14 |
| P27 Null | 34.2 ± 1.4 | 120.0 ± 22.7 | 4.10 ± 0.55 | 4.61 ± 0.94 |
| [b]P = | 0.02 | 0.20 | 0.50 | 0.10 |
| Spleen | | | | |
| Wildtype | 2.90 ± 0.61 | 135 ± 16.3 | 2.58 ± 0.24 | 1.03 ± 0.34 |
| P27 Null | 9.34 ± 0.54 | 400 ± 144 | 7.37 ± 0.86 | 3.11 ± 0.36 |
| P = | 0.001 | 0.05 | 0.05 | 0.02 |

[a]Total numbers of colony forming units per organ $\times 10^{-3}$.
[b]Statistics by Mann-Whitney test.

Western blots of normal murine ES cell extracts reveals p27 expression even at this early stage of mouse development. Western blots detected p27 expression in normal mouse tissues, including a diffuse pattern of expression in thymic tissue. No detectable p27 expression was seen in Western blots of tissues from knock-out mice.

Although the foregoing invention has been described in some detail by way of illustration and example for purposes of clarity of understanding, it will be obvious that certain changes and modifications may be practiced within the scope of the appended claims.

What is claimed is:

1. A transgenic mouse whose genome comprises a homozygous disruption of the endogenous cyclin inhibitor p27 gene locus, wherein said disruption results in the functional inactivation of the p27 gene, and wherein said mouse exhibits tissue hypertrophy relative to a mouse whose genome comprises the functional endogenous cyclin inhibitor p27 gene.

2. The hypertrophic mouse according to claim 1, wherein the p27 gene is replaced with a replacement gene.

3. The hypertrophic mouse according to claim 2, wherein the replacement gene comprises a neomycin resistance gene, a Herpes simplex virus thymidine kinase gene, or a gpt gene.

4. The hypertrophic mouse according to claim 1, wherein the endogenous p27 gene is partially replaced with a corresponding portion of a heterologous p27 gene that is functionally inactivated.

5. The hypertrophic mouse according to claim 1, wherein all or a portion of the p27 gene is deleted.

6. The hypertrophic mouse according to claim 1, wherein the p27 gene is functionally inactivated by integration at the p27 gene locus with a targeting construct comprising at least a portion of a sequence substantially homologous to a sequence present in or flanking the p27 gene locus.

7. The hypertrophic mouse according to claim 1, wherein the p27 gene is functionally inactivated by an insertion comprising a replacement sequence.

8. The hypertrophic mouse according to claim 1, wherein the p27 gene is functionally inactivated by a site-specific point mutation.

* * * * *